United States Patent
Hayashi et al.

(10) Patent No.: US 9,221,952 B2
(45) Date of Patent: Dec. 29, 2015

(54) LINEAR AND CYCLIC SILOXANES AND COSMETIC COMPOSITIONS MADE THEREOF

(75) Inventors: Akito Hayashi, Ichihara (JP); Tomohiro Iimura, Sodegaura (JP); Haruhiko Furukawa, Chiba (JP); Hidetoshi Kondo, Chiba (JP)

(73) Assignee: DOW CORNING TORAY CO., LTD., Chiyoda-Ku, Tokyo (JP)

( * ) Notice: Subject to any disclaimer, the term of this patent is extended or adjusted under 35 U.S.C. 154(b) by 0 days.

(21) Appl. No.: 13/513,080

(22) PCT Filed: Dec. 2, 2010

(86) PCT No.: PCT/JP2010/072067
§ 371 (c)(1),
(2), (4) Date: May 31, 2012

(87) PCT Pub. No.: WO2011/068250
PCT Pub. Date: Jun. 9, 2011

(65) Prior Publication Data
US 2012/0237583 A1    Sep. 20, 2012

(30) Foreign Application Priority Data
Dec. 3, 2009    (JP) .................. 2009-275675

(51) Int. Cl.
| | | |
|---|---|---|
| C08G 77/04 | (2006.01) | |
| A61K 8/58 | (2006.01) | |
| A61Q 19/00 | (2006.01) | |
| C07F 7/08 | (2006.01) | |
| A61Q 1/02 | (2006.01) | |
| A61Q 1/04 | (2006.01) | |
| A61Q 5/06 | (2006.01) | |
| A61Q 15/00 | (2006.01) | |
| A61Q 17/04 | (2006.01) | |

(52) U.S. Cl.
CPC .............. *C08G 77/045* (2013.01); *A61K 8/585* (2013.01); *A61Q 19/00* (2013.01); *C07F 7/0841* (2013.01); *C07F 7/0856* (2013.01); *A61Q 1/02* (2013.01); *A61Q 1/04* (2013.01); *A61Q 5/06* (2013.01); *A61Q 15/00* (2013.01); *A61Q 17/04* (2013.01)

(58) Field of Classification Search
CPC ........... A61Q 19/00; A61Q 1/02; A61Q 1/10; A61Q 17/04; A61Q 1/06; A61Q 15/00; A61Q 19/001; A61Q 19/007; A61K 8/891
See application file for complete search history.

(56) References Cited

U.S. PATENT DOCUMENTS

| | | |
|---|---|---|
| 4,980,167 A | 12/1990 | Harashima et al. |
| 5,623,017 A | 4/1997 | Hill |
| 5,628,989 A | 5/1997 | Harashima et al. |
| 5,654,362 A | 8/1997 | Schulz, Jr. et al. |
| 5,863,970 A | 1/1999 | Ghoshal et al. |
| 5,939,478 A | 8/1999 | Beck et al. |
| 6,238,656 B1 | 5/2001 | Morita et al. |
| 7,482,419 B2 | 1/2009 | Caprasse et al. |
| 7,563,452 B2 | 7/2009 | Kuroda et al. |
| 2002/0114771 A1* | 8/2002 | Nakanishi ................. 424/70.12 |
| 2004/0138373 A1* | 7/2004 | Hamachi et al. ............. 524/588 |
| 2004/0197284 A1* | 10/2004 | Auguste .................... 424/70.12 |
| 2006/0280712 A1 | 12/2006 | Kuroda et al. |

FOREIGN PATENT DOCUMENTS

| | | | |
|---|---|---|---|
| JP | 2-243612 A | | 9/1990 |
| JP | 5-279373 A | | 10/1993 |
| JP | 05279373 A | * | 10/1993 |
| JP | 8-012524 A | | 1/1996 |
| JP | 8-012545 A | | 1/1996 |
| JP | 8-012546 A | | 1/1996 |
| JP | 2627383 B2 | * | 7/1997 |
| JP | 9-241511 A | | 9/1997 |
| JP | 10-036219 A | | 2/1998 |
| JP | 11-193331 A | | 7/1999 |
| JP | 2000-063225 A | | 2/2000 |
| JP | 2000-281523 A | | 10/2000 |
| JP | 2001519838 A | | 10/2001 |
| JP | 2006213730 A | | 8/2006 |
| JP | 2006-522066 A | | 9/2006 |
| JP | 2006522066 A | | 9/2006 |

(Continued)

OTHER PUBLICATIONS

Rolando et al (Ring Formation in Linear Stepwise Polymerization, 1987, Macromolecules, vol. 20, pp. 2707-2713).*

(Continued)

*Primary Examiner* — Sean Basquill
*Assistant Examiner* — Mark V Stevens
(74) *Attorney, Agent, or Firm* — Howard & Howard Attorneys PLLC

(57) ABSTRACT

The present invention relates to a novel organopolysiloxane having a specified structure and a cosmetic containing the aforementioned organopolysiloxane. The novel organopolysiloxane according to the present invention is volatile, possesses stability at low temperature, provides superior glossiness, and has a superior property with respect to miscibility with a UV-ray absorber, and which is useful as a replacement of octamethylcyclotetrasiloxane, decamethylcyclopentasiloxane, or methyltrimethicone. The cosmetic according to the present invention can provide superior feeling to the touch during use and a superior outer appearance. Furthermore, a degree of freedom in blending various components such as UV-ray absorbers into the cosmetic according to the present invention is increased.

21 Claims, No Drawings

(56) References Cited

FOREIGN PATENT DOCUMENTS

| JP | 2007-532754 A | 11/2007 |
|---|---|---|
| JP | 4009382 B2 | 11/2007 |
| WO | WO 01/15658 A1 | 3/2001 |

OTHER PUBLICATIONS

M.R. Silicone Industries website, Silicone Oil (All viscosity), copyright 2010.*
Repko et al. (Hydrothermal preparation of hydrophobic and hydrophilic nanoparticles of iron oxide and a modification with CM-dextran, 2013, Journal of Nanoparticle Research, vol. 15, pp. 1-9).*
English language abstract for JP 2-243612 extracted from the espacenet.com database on Jul. 3, 2012, 10 pages.
English language abstract for JP 4009382 extracted from the espacenet.com and the English language translation extracted from the PAJ database on Jul. 5, 2012, 112 pages.
English language abstract and translation for JP 5-279373 extracted from the PAJ database on Jul. 9, 2012, 26 pages.
English language abstract and translation for JP 8-012524 extracted from the PAJ database on Jul. 5, 2012, 28 pages.
English language abstract for JP 8-012524 extracted from the espacenet.com database on Jul. 3, 2012, 7 pages.
English language abstract and translation for JP 8-012546 extracted from the PAJ database on Jul. 3, 2012, 26 pages.
English language abstract and translation for JP 9-241511 extracted from the PAJ database on Jul. 5, 2012, 29 pages.
English language abstract and translation for JP 10-036219 extracted from the PAJ database on Jul. 5, 2012, 37 pages.
English language abstract for JP 11-193331 extracted from the espacenet.com database on Jul. 5, 2012, 15 pages.
English language abstract and translation for JP 2000-063225 extracted from the PAJ database on Jul. 5, 2012, 61 pages.
English language abstract for JP 2000-281523 extracted from the espacenet.com database on Jul. 5, 2012, 24 pages.
English language abstract not available for JP 2007-532754; however, see English language equivalent U.S. Pat. No. 7,482,419. Original document extracted from the espacenet.com database on Jul. 5, 2012, 39 pages.
English language abstract for WO 01/15658 extracted from the espacenet.com database on Jul. 5, 2012, 83 pages.
Masaaki Amako et al., "Siloxane-supported organometallic compounds and their catalytic activities for the hydrosilylation of vinylsilanes and dienes", Dalton Trans., 2005, pp. 74-81.
Heinz-Peter Schuchmann et al., "Photolysis at lambda 185 nm of hexamethyldisiloxane in the liquid phase", Journal of Organometallic Chemistry, vol. 148, 1978, pp. 213-223.
Gaelle Baquey et al., "Decomposition of Di-tert-butyl Peroxide in Siloxane: An Approach of the Free Radical Cross-Linking of Silicones", Macromolecules, vol. 38, 2005, pp. 9571-9583.
Richard J. Rolando et al., "Ring Formation in Linear Stepwise Polymerization", Macromolecules, vol. 20, 1987, pp. 2707-2713.
Golesworthy R.C. et al., Chemical Abstracts for: "Chemical reactions under the influence of an electrical discharge. I. The action of the discharge on hexamethyldisiloxane and tetramethylsilane", vol. 54, No. 3, 1960, and "Chemical reactions under the influence of an electrical discharge", Proceedings of the Royal Society of London, Series A: Mathematical, Physical, and Engineering Sciences, vol. 292, 1966. 2 pages.
International Search Report for Application No. PCT/JP2010/072067 dated May 13, 2011, 5 pages.
English language abstract not found for JP2006522066; however, see English language equivalent U.S. 2004/0197284. Original document extracted from espacenet.com database on May 17, 2014, 27 pages.
English language abstract not found for JP2001519838; however, see English language equivalent U.S. Pat. No. 5,863,970. Original document extracted from the espacenet.com database on Apr. 17, 2014, 68 pages.
English language abstract and machine-assisted English translation for JP2006213730 extracted from the PAJ database on Apr. 17, 2014, 121 pages.
English language abstract for JP2006522066 extracted from the espacenet.com database on Apr. 17, 2014, 27 pages.

* cited by examiner

LINEAR AND CYCLIC SILOXANES AND COSMETIC COMPOSITIONS MADE THEREOF

TECHNICAL FIELD

The present invention relates to a novel organopolysiloxane having a specified structure, as well as a cosmetic containing the aforementioned organopolysiloxane.

This application claims priority to and all the advantages of International Patent Application No. PCT/JP2010/072067, filed on Dec. 2, 2010, which claims priority to Japanese Patent Application No. JP 2009-275675, filed on Dec. 3, 2009.

BACKGROUND ART

Conventionally, as volatile components (oil agents) composing a cosmetic, cyclic polysiloxanes such as octamethylcyclotetrasiloxane (hereinafter, referred to as "D4"), decamethylcyclopentasiloxane (hereinafter, referred to as "D5") and the like have been used. However, while D4 exhibits superior volatility, in the case of storing a cosmetic containing D4 at low temperature, D4 is crystallized, and for this reason, there is a problem in that the sensation during use is remarkably impaired. On the other hand, D5 has no problems in storage stability at low temperature, but the volatility thereof is insufficient, and for this reason, there is a problem in that good sensation during use in a cosmetic containing D5 cannot be obtained, such that feeling to touch is heavy during use, stickiness is exhibited, and a dry feeling occurs on skin or hair to which it is applied, and the like.

Considering the aforementioned problems, WO 01/15658 proposes a cosmetic containing an organopolysiloxane represented by $\{(CH_3)_3SiO\}_3SiCH_3$ (hereinafter, referred to as "methyltrimethicone") as a volatile component.

However, while the cosmetic blending the organopolysiloxane described in WO 01/15658 exhibits superior volatility, feeling to the touch during use cannot be sufficiently improved, and in particular, the problem of a dry feeling cannot be sufficiently prevented. In addition, the compounds described in WO 01/15658 have a low miscibility with respect to a UV-ray absorber, and for this reason, a large amount of other oil agents must be blended in the cosmetic in order to dissolve the UV-ray absorber, thereby causing many restrictions with respect to components and compositions of cosmetics. Therefore, further improvements with respect to the aforementioned points are needed.

DISCLOSURE OF INVENTION

Technical Problems

A first objective of the present invention is to provide a novel organopolysiloxane which is volatile, possesses stability at low temperature, provides superior glossiness, and has a superior property with respect to miscibility with a UV-ray absorber, as well as is useful as a replacement of D4, D5 or methyltrimethicone.

A second objective of the present invention is to provide a cosmetic in which superior feeling to the touch during use is exhibited, a superior outer appearance is provided, and a degree of freedom in blending various components such as UV-ray absorbers is increased.

Technical Solution

The first object of the present invention can be achieved by an organopolysiloxane represented by the following general formula (1) or (2):

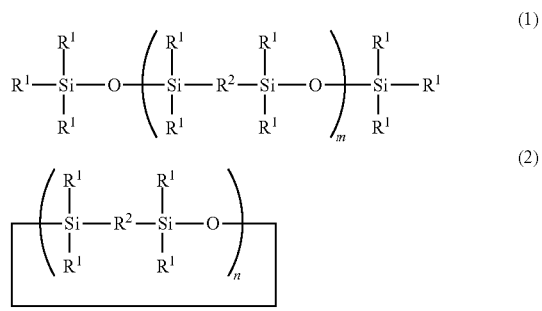

wherein
each $R^1$ is independently a substituted or non-substituted, and linear, branched or cyclic monovalent hydrocarbon group having 1 to 30 carbon atoms and containing no aliphatic unsaturated bond;
$R^2$ is a substituted or non-substituted, and linear or branched divalent hydrocarbon group having 1 to 30 carbon atoms and containing no aliphatic unsaturated bond;
m is an integer ranging from 1 to 4; and
n is an integer ranging from 2 to 4. The aforementioned $R^2$ is preferably a dimethylene group.

The organopolysiloxane represented by the aforementioned general formula (1) or (2) can be produced via a step of hydrolyzing an organosilicon compound represented by the following structural formula:

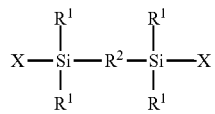

wherein
$R^1$ and $R^2$ are the same as defined above; and
X is a chlorine atom, a hydroxyl group or an alkoxy group having 1 to 3 carbon atoms. In particular, it is preferable for the process producing the above organopolysiloxane to comprise a step of hydrolyzing an organosilicon compound represented by the following structural formula:

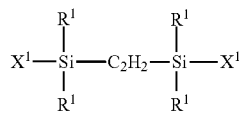

wherein
$R^1$ is the same as defined above; and $X^1$ is a chlorine atom or a methoxy group.

The second objective of the present invention can be achieved by a cosmetic comprising the organopolysiloxane represented by the aforementioned general formula (1) or (2).

The cosmetic of the present invention can contain both the organopolysiloxane represented by the aforementioned general formula (1) and the organopolysiloxane represented by the aforementioned general formula (2).

The blending amount of the aforementioned organopolysiloxane in the cosmetic of the present invention may range from 1 to 99% by weight with respect to the total amount of the cosmetic.

The cosmetic of the present invention can further comprise at least one oil agent other than the aforementioned organopolysiloxane.

The aforementioned oil agent may be a silicone oil, and the aforementioned silicone oil can be a hydrophobic silicone oil having a viscosity at 25° C. ranging from 0.65 to 100,000 mm²/s.

In addition, the aforementioned silicone oil can be an organopolysiloxane represented by the following general formula (3), (4) or (5):

$$(CH_3)_a Si\text{—}O\text{—}(\underset{\underset{CH_3}{|}}{\overset{\overset{CH_3}{|}}{Si}}\text{—}O)_b\text{—}(\underset{\underset{CH_3}{|}}{\overset{\overset{R^3}{|}}{Si}}\text{—}O)_c\text{—}Si(CH_3)_a \tag{3}$$

with $R^3_{(3-a)}$ groups on the terminal silicons wherein
$R^3$ is a hydrogen atom, a hydroxyl group or a group selected from monovalent non-substituted or fluorine- or amino-substituted, $C_{1-30}$ alkyl groups, aryl groups, alkoxy groups and groups represented by $(CH_3)_3SiO\{(CH_3)_2SiO\}_1 Si(CH_3)_2CH_2CH_2$—, wherein 1 is an integer ranging from 0 to 1,000;
a is an integer ranging from 0 to 3;
b is an integer ranging from 0 to 1,000; and
c is an integer ranging from 0 to 1,000, with the proviso that $1 \le b+c \le 2,000$, $$\left[\underset{\underset{CH_3}{|}}{\overset{\overset{CH_3}{|}}{Si}}\text{—}O\right]_d \left[\underset{\underset{CH_3}{|}}{\overset{\overset{R^3}{|}}{Si}}\text{—}O\right]_e \tag{4}$$

wherein
$R^3$ is the same as defined above;
d is an integer ranging from 0 to 8; and
e is an integer ranging from 0 to 8, with the proviso that $3 \le d+e \le 8$, $$R^3_{(4-f)}Si(OSiCH_3)_g \tag{5}$$

wherein
$R^3$ is the same as defined above;
f is an integer ranging from 1 to 4; and
g is an integer ranging from 0 to 500.

The cosmetic of the present invention can further comprise at least one surfactant selected from the group consisting of anionic surfactants, cationic surfactants, nonionic surfactants and amphoteric surfactants.

The cosmetic of the present invention can further comprise powder and/or a coloring agent. The aforementioned powder can be at least one type of powder selected from the group consisting of inorganic pigment powder, organic pigment powder and resin powder, having an average particle size ranging from 1 nm to 20 μm. At least one part of the aforementioned powder and/or the aforementioned coloring agents may be subjected to a water-repellent treatment.

The cosmetic of the present invention can further comprise at least one material selected from the group consisting of water-soluble polymers, oil-soluble gelling agents and organo-modified clay minerals.

The cosmetic of the present invention can further comprise at least one material selected from the group consisting of silicone resins, silicone elastomers and organo-modified silicones.

The cosmetic of the present invention can further comprise a UV-ray protective component.

The present invention also relates to a skin care product, a hair product, an antiperspirant product, a deodorant product, a makeup product or a UV-ray protective product, containing the aforementioned cosmetic.

Advantageous Effects of Invention

The organopolysiloxane of the present invention has a low degree of polymerization, is volatile, exhibits superior stability at low temperature, provides superior glossiness in the case of blending in a cosmetic, and possesses superior miscibility with various organic compounds such as other oil agents, UV-ray absorbers and the like. In addition, the organopolysiloxane of the present invention can be easily synthesized. Therefore, the organopolysiloxane the present invention is useful as a replacement for D4, D5 or methyltrimethicone.

The cosmetic of the present invention exhibits superior feeling to the touch during use, provides superior outer appearance, and has an increased degree of freedom of blending various components such as UV-ray absorbers and the like. In particular, in the case of using as a skin cosmetic such as an antiperspirant product, the cosmetic is useful since a dry feeling is remarkably prevented, as compared to the case in which a conventional volatile oil agent is used.

BEST MODES FOR CARRYING OUT THE INVENTION

The organopolysiloxane of the present invention is represented by the following general formula (1) or (2):

$$R^1\text{—}\underset{\underset{R^1}{|}}{\overset{\overset{R^1}{|}}{Si}}\text{—}O\text{—}\left(\underset{\underset{R^1}{|}}{\overset{\overset{R^1}{|}}{Si}}\text{—}R^2\text{—}\underset{\underset{R^1}{|}}{\overset{\overset{R^1}{|}}{Si}}\text{—}O\right)_m\text{—}\underset{\underset{R^1}{|}}{\overset{\overset{R^1}{|}}{Si}}\text{—}R^1 \tag{1}$$

$$\left[\underset{\underset{R^1}{|}}{\overset{\overset{R^1}{|}}{Si}}\text{—}R^2\text{—}\underset{\underset{R^1}{|}}{\overset{\overset{R^1}{|}}{Si}}\text{—}O\right]_n \tag{2}$$

wherein
each $R^1$ is independently a substituted or non-substituted, and linear, branched or cyclic monovalent hydrocarbon group having 1 to 30 carbon atoms and containing no aliphatic unsaturated bond;
$R^2$ is a substituted or non-substituted, and linear or branched divalent hydrocarbon group having 1 to 30 carbon atoms and containing no aliphatic unsaturated bond
m is an integer ranging from 1 to 4, is preferably 1 or 2, and is more preferably 1; and
n is an integer ranging from 2 to 4, is preferably 2 or 3 and is more preferably 2.

As examples of the substituted or non-substituted, and linear, branched or cyclic monovalent hydrocarbon group having 1 to 30 carbon atoms and containing no aliphatic unsaturated bond, mention may be made of, for example, linear or branched alkyl groups having 1 to 30 carbon atoms such as a methyl group, an ethyl group, a propyl group, a butyl group, a pentyl group, a hexyl group, a heptyl group, an octyl group, a decyl group, a dodecyl group and the like; cycloalkyl groups having 3 to 30 carbon atoms such as a cyclopentyl group, a cyclohexyl group and the like; aryl groups having 6 to 30 carbon atoms such as a phenyl group, a tolyl group, a xylyl group, a naphthyl group and the like; aralkyl groups having 7 to 30 carbon atoms such as a benzyl group, a phenethyl group and the like; and substituted groups thereof in which hydrogen atoms bonded to carbon atoms of the aforementioned groups are at least partially substituted by a halogen atom such as a fluorine atom or the like, or an organic group containing a carbinol group, an epoxy group, a glycidyl group, an acyl group, a carboxyl group, an amino group, a methacryl group, a mercapto group, an amide group, an oxyalkylene group or the like. The monovalent hydrocarbon group is preferably a non-substituted monovalent hydrocarbon group having 1 to 30 carbon atoms, and more preferably a non-substituted monovalent hydrocarbon group having 1 to 6 carbon atoms. In particular, a methyl group, an ethyl group, or a phenyl group is preferred.

As examples of the substituted or non-substituted, and linear or branched divalent hydrocarbon group having 1 to 30 carbon atoms and containing no aliphatic unsaturated bond, mention may be made of, for example, linear or branched alkylene groups having 1 to 30 carbon atoms such as a methylene group, a dimethylene group, a trimethylene group, a tetramethylene group, a pentamethylene group, a hexamethylene group, a heptamethylene group, an octamethylene group and the like; arylene groups having 6 to 30 carbon atoms such as a phenylene group, a diphenylene group and the like; alkylenearylene groups having 7 to 30 carbon atoms such as a dimethylenephenylene group and the like; and substituted groups thereof in which hydrogen atoms bonded to carbon atoms of the aforementioned groups are at least partially substituted by a halogen atom such as a fluorine atom or the like, or an organic group containing a carbinol group, an epoxy group, a glycidyl group, an acyl group, a carboxyl group, an amino group, a methacryl group, a mercapto group, an amide group, an oxyalkylene group or the like. The divalent hydrocarbon group is preferably a non-substituted divalent hydrocarbon group having 1 to 30 carbon atoms, more preferably a linear or branched alkylene group having 1 to 6 carbon atoms, and in particular, preferably a linear alkylene group having 1 to 6 carbon atoms. The most preferable example of the aforementioned $R^2$ is a dimethylene group (ethylene group), a trimethylene group, or a tetramethylene group.

As examples of the aforementioned aliphatic unsaturated groups, mention may be made of, for example, alkenyl groups having 2 to 10 carbon atoms such as a vinyl group, an allyl group, a butenyl group, a hexenyl group, an octenyl group and the like.

The organopolysiloxanes represented by the aforementioned general formula (1) or (2) possess volatility. The term volatility used herein means that a vapor pressure of other than 0 is exhibited under one atom at 25° C., and for example, a vapor pressure ranging from 0.13 Pa to 40,000 Pa (from $10^{-3}$ to 300 mmHg is exhibited. In addition, the organopolysiloxanes represented by the aforementioned general formula (1) or (2) are liquid at room temperature (25° C.), and are preferably colorless and transparent.

The organopolysiloxane represented by the aforementioned general formula (1) or (2) can be easily synthesized, and for example, can be prepared by means of the process (A) or (B) described below using an organosilicon compound represented by the following structural formula as a raw material.

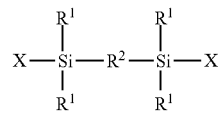

wherein $R^1$ and $R^2$ are the same groups as defined above, and the preferable groups thereof are also the same as described above; and X is a chlorine atom, a hydroxyl group or an alkoxy group having 1 to 3 carbon atoms. In view of reactivity during the hydrolysis reaction and availability, X is, in particular, preferably a chlorine atom or a methoxy group.

(A) A chloride corresponding to the desired organopolysiloxane (in the aforementioned structural formula, X is a chlorine atom) is hydrolyzed. Thereby, an organopolysiloxane represented by general formula (2) is obtained. Subsequently, in the presence of an excess of hexamethyldisiloxane and an acid catalyst, equilibration is carried out. Thereby, an organopolysiloxane of general formula (1) can be obtained. As examples of the aforementioned chloride, mention may be made of, for example, a dichloride such as a compound of the following formula (6):

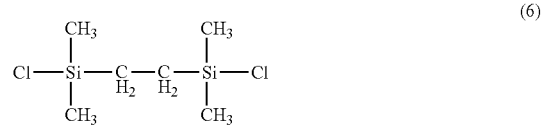

and the like.

(B) An alkoxide corresponding to the desired organopolysiloxane, in which in the aforementioned structural formula, X is an alkoxy group having 1 to 3 carbon atoms, is treated in the presence of an excess of hexamethyldisiloxane and an acid catalyst. Thereby, an organopolysiloxane of general formula (1) can be obtained. A carboxylic acid or an alcohol is included in the reaction system, if necessary. As examples of the aforementioned alkoxide, mention may be made of, for example, a dialkoxide of the following formula (7):

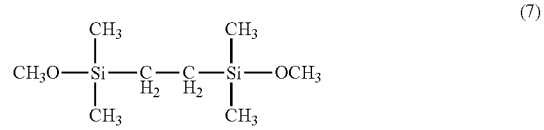

and the like.

The organopolysiloxane of the present invention is volatile, is stable at low temperature, provides superior glossiness, and possesses superior miscibility with various organic compounds such as UV-ray absorbers, other oil agents and the like. In addition, problems of crystallization or coagulation do not occur even in the case of storing at low temperature, and superior stability at low temperature is exhibited. Therefore, the organopolysiloxane of the present invention is useful as a replacement of conventional volatile silicones such as D4, D5 or methyltrimethicone.

The organopolysiloxane of the present invention can be preferably blended in a cosmetic. In the cosmetic of the present invention, at least one of the organopolysiloxane of general formula (1) and the organopolysiloxane of general formula (2) can be blended, and both organopolysiloxanes described above may also be blended therein.

The blending amount of the aforementioned organopolysiloxane in the cosmetic of the present invention is not particularly restricted. The cosmetic of the present invention can contain the organopolysiloxane, for example, in an amount ranging from 1 to 99% by weight on the basis of the total weight of the cosmetic. More particularly, the blending amount of the aforementioned organopolysiloxane can suitably vary, for example, in the range of 10 to 90% by weight, 20 to 80% by weight, or 30 to 70% by weight, depending on the type of the cosmetic.

The cosmetic of the present invention may further comprise at least one oil agent other than the aforementioned organopolysiloxane. As examples of oil agents, mention may be made of animal oils, vegetable oils, synthetic oils and the like, which are generally used in cosmetics. The aforementioned oil agents may be derived from any origins, may be in the form of a solid, a semi-solid, or a liquid, and may be non-volatile, semi-volatile or volatile, as long as they are hydrophobic. More particularly, as examples thereof, mention may be made of hydrocarbons, fats and oils, waxes, hardened oils, fatty acid ester oils, higher fatty acids, silicone oils, fluorine-based oils, lanolin derivatives, higher alcohols and the like. The oil agents are used in order to provide lubricity to skin or hair, make skin flexible, and provide a moisturizing sensation.

As the aforementioned oil agents, silicone oils are preferred. The silicone oils are hydrophobic as they are oil agents, and the molecular structure thereof may be a cyclic, linear or branched structure. The viscosity of the silicone oils at 25° C. usually ranges from 0.65 to 100,000 mm$^2$/s and preferably ranges from 0.65 to 10,000 mm$^2$/s.

As examples of the aforementioned silicone oils, mention may be made of cyclic organopolysiloxanes, linear organopolysiloxanes, and branched organopolysiloxanes. Among these, volatile linear organopolysiloxanes, branched organopolysiloxanes, and cyclic organopolysiloxanes are preferred.

As the aforementioned silicone oils, for example, organopolysiloxanes represented by the following general formula (3), (4) or (5):

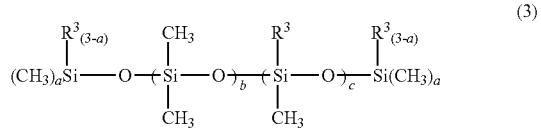

(3)

wherein
R$^3$ is a hydrogen atom, a hydroxyl group or a group selected from monovalent non-substituted or fluorine- or amino-substituted, C$_{1-30}$ alkyl groups, aryl groups, alkoxy groups and groups represented by (CH$_3$)$_3$SiO{(CH$_3$)$_2$SiO}$_1$Si(CH$_3$)$_2$CH$_2$CH$_2$—, wherein 1 is an integer ranging from 0 to 1,000;

a is an integer ranging from 0 to 3;

b is an integer ranging from 0 to 1,000; and c is an integer ranging from 0 to 1,000, with the proviso that 1≤b+c≤2,000,

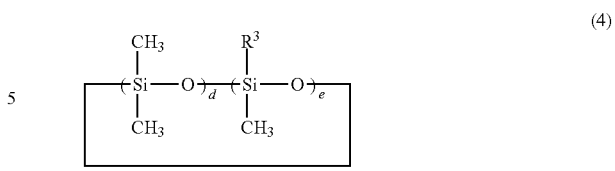

(4)

wherein
R$^3$ is the same as defined above;
d is an integer ranging from 0 to 8; and
e is an integer ranging from 0 to 8, with the proviso that 3≤d+e≤8,

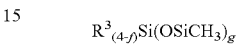

(5)

wherein
R$^3$ is the same as defined above;
f is an integer ranging from 1 to 4; and
g is an integer ranging from 0 to 500, can be used.

As examples of non-substituted or fluorine- or amino-substituted alkyl groups, aryl groups, and alkoxy groups having 1 to 30 carbon atoms, mention may be made of, for example, linear or branched alkyl groups having 1 to 30 carbon atoms such as a methyl group, an ethyl group, a propyl group, a butyl group, a pentyl group, a hexyl group, a heptyl group, an octyl group, a decyl group, a dodecyl group and the like; cycloalkyl groups having 3 to 30 carbon atoms such as a cylopentyl group, a cyclohexyl group and the like; aryl groups having 6 to 30 carbon atoms such as a phenyl group, a tolyl group, a xylyl group, a naphthyl group and the like; alkoxy groups having 1 to 30 carbon atoms such as a methoxy group, an ethoxy group, a propoxy group and the like; and substituted groups thereof, in which hydrogen atoms bonded to carbon atoms of the aforementioned groups are at least partially substituted by a fluorine atom or an amino group. A non-substituted alkyl group or aryl group is preferred, and a non-substituted alkyl group or aryl group having 1 to 6 carbon atoms or aryl group is further preferred. A methyl group, an ethyl group or a phenyl group is, in particular, preferred.

More particularly, as examples of cyclic organopolysiloxanes, mention may be made of hexamethylcyclotrisiloxane (D3), octamethylcyclotetrasiloxane (D4), decamethylcyclopentasiloxane (D5), dodecamethylcyclohexasiloxane (D6), 1,1-diethylhexamethylcyclotetrasiloxane, phenylheptamethylcyclotetrasiloxane, 1,1-diphenylhexamethylcyclotetrasiloxane, 1,3,5,7-tetravinyltetramethylcyclotetrasiloxane, 1,3,5,7-tetramethylcyclotetrasiloxane, 1,3,5,7-tetracyclohexyltetramethylcyclotetrasiloxane, tris(3,3,3-trifluoropropyl)trimethylcyclotrisiloxane, 1,3,5,7-tetra(3-methacryloxypropyl)tetramethylcyclotetrasiloxane, 1,3,5,7-tetra(3-acryloxypropyl)tetramethylcyclotetrasiloxane, 1,3,5,7-tetra(3-carboxypropyl)tetramethylcyclotetrasiloxane, 1,3,5,7-tetra(3-vinyloxypropyl)tetramethylcyclotetrasiloxane, 1,3,5,7-tetra(p-vinylphenyl)tetramethylcyclotetrasiloxane, 1,3,5,7-tetra[3-(p-vinylphenyl)propyl]tetramethylcyclotetrasiloxane, 1,3,5,7-tetra(N-acryloyl-N-methyl-3-aminopropyl)tetramethylcyclotetrasiloxane, 1,3,5,7-tetra(N,N-bis(lauroyl)-3-aminopropyl)tetramethylcyclotetrasiloxane and the like.

As examples of linear organopolysiloxanes, mention may be made of a dimethylpolysiloxane in which both molecular terminals are capped with trimethylsiloxy groups (dimethylsilicone with a low viscosity such as 2 cst or 6 cst to dimethylsilicone with a high viscosity such as 1,000,000 cst), an organohydrogenpolysiloxane, a methylphenylpolysiloxane in which both molecular terminals are capped with trimethylsiloxy groups, a copolymer of methylphenylsiloxane and dimethylsiloxane in which both molecular terminals are capped with trimethylsiloxy groups, a diphenylpolysiloxane in which both molecular terminals are capped with trimethylsiloxy groups, a copolymer of diphenylsiloxane and dimethylsiloxane in which both molecular terminals are capped with trimethylsiloxy groups, a trimethylpentaphenyltrisiloxane, a phenyl(trimethylsiloxy)siloxane, a methylalkylpolysiloxane in which both molecular terminals are capped with trimethylsiloxy groups, a copolymer of methylalkylsiloxane and dimethylpolysiloxane in which both molecular terminals are capped with trimethylsiloxy groups, a copolymer of methyl(3,3,3-trifluoropropyl)siloxane and dimethylsiloxane in which both molecular terminals are capped with trimethylsiloxy groups, an α,ω-dihydroxypolydimethylsiloxane, an α,ω-diethoxypolydimethylsiloxane, a 1,1,1,3,5,5,5-heptamethyl-3-octyltrisiloxane, a 1,1,1,3,5,5,5-heptamethyl-3-dodecyltrisiloxane, a 1,1,1,3,5,5,5-heptamethyl-3-hexadecyltrisiloxane, a tristrimethylsiloxymethylsilane, a tristrimethylsiloxyalkylsilane, a tetrakistrimethylsiloxysilane, tetramethyl-1,3-dihydroxydisiloxane, an octamethyl-1,7-dihydroxytetrasiloxane, a hexamethyl-1,5-diethoxytrisiloxane, a hexamethyldisiloxane, an octamethyltrisiloxane, a higher alkoxy-modified silicone, a higher fatty acid-modified silicone and the like.

As examples of branched organopolysiloxanes, mention may be made of methyltristrimethylsiloxysilane, ethyltristrimethylsiloxysilane, propyltristrimethylsiloxysilane, tetrakistrimethylsiloxysilane, phenyltristrimethylsiloxysilane and the like.

When at least one of the aforementioned silicone oils is contained in the cosmetic of the present invention, stability of the cosmetic over time can be improved, and a refreshing feeling to the touch which the silicone oils inherently possess can be realized.

The oil agents other than the silicone oils are preferably in the form of a liquid at 5 to 100° C. As the oil agents other than the silicone oils, hydrocarbon oils and/or fatty acid ester oils are preferred. They may be used alone, but preferably used in combination with the aforementioned silicone oils. By using the aforementioned silicone oils in combination with the hydrocarbon oils and/or fatty acid ester oils, advantages can be obtained in that moisture on the skin can be maintained, and a moisturizing sensation (also referred to as "moisturizing feeling to the touch") such as moisturizing skin or hair and smooth feeling to the touch, in addition to the refreshing feeling to the touch which the silicone oils inherently possess, can be provided in cosmetics, and stability over time of cosmetics is not impaired. In addition, use of the cosmetics containing the aforementioned silicone oils in combination with the hydrocarbon oils and/or fatty acid ester oils provides advantages in that these moisturizing components can be stably and uniformly applied on the skin or hair, the moisturizing effects of the moisturizing components on the skin are increased, and superior smoothness and moisturizing feeling can be provided as compared with cosmetics containing only oil agents other than silicone oils (the hydrocarbon oils and/or fatty acid ester oils).

In addition thereto, hydrocarbons, fats and oils, waxes, hardened oils, fatty acid ester oils, higher fatty acids, silicone oils, fluorine-based oils, lanolin derivatives, higher alcohols and the like may be used in combination of two or more types thereof. For example, the oil agents described below may be used in combination of two or more types. Hereinafter, the oil agents other than silicone oils which can be used in the present invention are described in detail.

As the oil agents other than the silicone oils, any one of solid, semi-solid, and liquid oil agents can be used as long as they are used in common cosmetics. As examples thereof, mention may be made of one or more types selected from hydrocarbon oils, ester oils, natural animal or vegetable fats and oils, semi-synthetic fats and oils, higher alcohols, higher fatty acids, fluorine-based oil agents, triglycerides, and synthetic sebum.

As examples of hydrocarbon oils, mention may be made of liquid paraffin, light liquid isoparaffin, heavy liquid isoparaffin, vaseline, n-paraffin, isoparaffin, isododecane, isohexadecane, polyisobutylene, hydrogenated polyisobutylene, polybutene, ozokerite, ceresin, microcrystalline wax, paraffin wax, polyethylene wax, polyethylene/polypropylene wax, squalane, squalene, pristane, polyisoprene and the like.

As examples of ester oils, mention may be made of hexyldecyl octanoate, cetyl octanoate, isopropyl myristate, isopropyl palmitate, butyl stearate, hexyl laurate, myristyl myristate, oleyl oleate, decyl oleate, octyldodecyl myristate, hexyldecyl dimethyloctanoate, cetyl lactate, myristyl lactate, diethyl phthalate, dibutyl phthalate, lanolin acetate, ethylene glycol monostearate, propylene glycol monostearate, propylene glycol dioleate, glyceryl monostearate, glyceryl monooleate, glyceryl tri-2-hexanoate, trimethylolpropane tri-2-ethylhexanoate, ditrimethylolpropane triethylhexanoate, ditrimethylolpropane isostearate/sebacate, trimethylolpropane trioctanoate, trimethylolpropane triisostearate, diisopropyl adipate, diisobutyl adipate, 2-hexyldecyl adipate, di-2-heptylundecyl adipate, diisostearyl malate, hydrogenated castor oil monoisostearate, N-alkylglycol monoisostearate, octyldodecyl isostearate, isopropyl isostearate, isocetyl isostearate, ethylene glycol di-2-ethylhexanoate, cetyl 2-ethylhexanoate, pentaerythritol tetra-2-ethylhexanoate, octyldodecyl gum ester, ethyl oleate, octyldodecyl oleate, neopentylglycol dicaprate, triethyl citrate, 2-ethylhexyl succinate, dioctyl succinate, isocetyl stearate, diisopropyl sebacate, di-2-ethylhexyl sebacate, diethyl sebacate, dioctyl sebacate, dibutyloctyl sebacate, cetyl palmitate, octyldodecyl palmitate, octyl palmitate, 2-ethylhexyl palmitate, 2-hexyldecyl palmitate, 2-heptylundecyl palmitate, cholesteryl 12-hydroxystearate, dipentaerythrityl fatty acid ester, 2-hexyldecyl myristate, ethyl laurate, 2-octyldodecyl N-lauroyl-L-glutamate, di(cholesteryl/behenyl/octyldodecyl) N-lauroyl-L-glutamate, di(cholesteryl/octyldodecyl) N-lauroyl-L-glutamate, di(phytosteryl/behenyl/octyldodecyl) N-lauroyl-L-glutamate, di(phytosteryl/octyldodecyl) N-lauroyl-L-glutamate, isopropyl N-lauroylsarcosinate, diisostearyl malate, neopentylglycol dioctanoate, isodecyl neopentanoate, isotridecyl neopentanoate, isostearyl neopentanoate, isononyl isononanoate, isotridecyl isononanoate, octyl isononanoate, isotridecyl isononanoate, diethylpentanediol dineopentanoate, methylpentanediol dineopentanoate, octyldodecyl neodecanoate, 2-butyl-2-ethyl-1,3-propanediol dioctanoate, pentaerythrityl tetraoctanoate, dipentaerythrityl hydrogenated rosin, pentaerythrityl triethylhexanoate, dipentaerythrityl (hydroxystearate/stearate/rosinate), polyglyceryl tetraisostearate, polyglyceryl-10 nonaisostearate, polyglyceryl-8 deca(erucate/isostearate/ricinoleate), (hexyldecanoic acid/sebacic acid) diglyceryl oligoester, glycol distearate (ethyleneglycol distearate), diisopropyl dimmer dilinoleate, diisostearyl dimmer dilinoleate, di(isostearyl/phytosteryl) dimmer dilinoleate, (phytosteryl/behenyl) dimmer dilinoleate, (phytosteryl/isostearyl/cetyl/stearyl/behenyl) dimmer dilinoleate, dimmer dilinoleyl dimmer dilinoleate, dimmer dilinoleyl diisostearate, dimmer dilinoleyl hydrogenated rosin condensate, dimmer dilinoleic acid hardened castor oil, hydroxyalkyl dimmer dilinoleyl ether, glyceryl triisooctanoate, glyceryl triisostearate, glyceryl trimyristate, glyceryl triisopalmitate, glyceryl trioctanoate, glyceryl trioleate, glyceryl diisostearate, glyceryl tri(caprylate/caprate), glyceryl tri(caprylate/caprate/myristate/stearate), hydrogenated rosin triglyceride (hydrogenated ester gum), rosin triglyceride (ester gum), glyceryl behenate eicosane dioate, glyceryl di-2-heptylundecanoate, diglyceryl myristate isostearate, cholesteryl acetate, cholesteryl nonanoate, cholesteryl stearate, cholesteryl isostearate, cholesteryl oleate, cholesteryl 12-hydroxystearate, cholesteryl ester of macadamia nut oil fatty acid, phytosteryl ester of macadamia nut oil fatty acid, phytosteryl isostearate, cholesteryl ester of soft lanolin fatty acid, cholesteryl ester of hard lanolin fatty acid, cholesteryl ester of long-chain branched fatty acid, cholesteryl ester of long-chain α-hydroxy fatty acid, octyldodecyl ricinoleate, octyldodecyl ester of lanolin fatty acid, octyldodecyl erucate, isostearic acid hardened castor oil, ethyl ester of avocado fatty acid, isopropyl ester of lanolin fatty acid, and the like.

As examples of natural animal or vegetable fats and oils and semi-synthetic fats and oils, mention may be made of avocado oil, linseed oil, almond oil, ibota wax, perilla oil, olive oil, cacao butter, kapok wax, kaya oil, carnauba wax, liver oil, candelilla wax, beef tallow, neat's-foot oil, beef bone fat, hydrogenated beef tallow, apricot kernel oil, spermaceti wax, hydrogenated oil, wheat germ oil, sesame oil, rice germ oil, rice bran oil, sugar cane wax, sasanqua oil, safflower oil, shear butter, Chinese tung oil, cinnamon oil, jojoba wax, olive oil, squalane, shellac wax, turtle oil, soybean oil, tea seed oil, camellia oil, evening primrose oil, corn oil, lard, rapeseed oil, Japanese tung oil, rice bran wax, germ oil, horse fat, persic oil, palm oil, palm kernel oil, castor oil, hydrogenated castor oil, castor oil fatty acid methyl ester, sunflower oil, grape oil, bayberry wax, jojoba oil, hydrogenated jojoba ester, macadamia nut oil, beeswax, mink oil, cottonseed oil, cotton wax, Japanese wax, Japanese wax kernel oil, montan wax, coconut oil, hydrogenated coconut oil, tri-coconut oil fatty acid glyceride, mutton tallow, peanut oil, lanolin, liquid lanolin, reduced lanolin, lanolin alcohol, hard lanolin, lanolin acetate, lanolin fatty acid isopropyl ester, POE lanolin alcohol ether, POE lanolin alcohol acetate, lanolin fatty acid polyethylene glycol, POE hydrogenated lanolin alcohol ether, egg yolk oil and the like, with the proviso that POE means polyoxyethylene.

As examples of higher alcohols, mention may be made of lauryl alcohol, myristyl alcohol, palmityl alcohol, stearyl alcohol, behenyl alcohol, hexadecyl alcohol, oleyl alcohol, isostearyl alcohol, hexyldodecanol, octyldodecanol, cetostearyl alcohol, 2-decyltetradecinol, cholesterol, sitosterol, phytosterol, lanosterol, POE cholesterol ether, monostearyl glycerol ether (batyl alcohol), monooleyl glyceryl ether (selachyl alcohol) and the like.

As examples of higher fatty acids, mention may be made of, for example, lauric acid, myristic acid, palmitic acid, stearic acid, behenic acid, undecylenic acid, oleic acid, linolic acid, linolenic acid, arachidonic acid, eicosapentaenoic acid (EPA), docosahexaenoic acid (DHA), isostearic acid, 12-hydroxystearic acid, and the like.

As examples of fluorine-based oils, mention may be made of perfluoro polyether, perfluorodecalin, perfluorooctane and the like. The aforementioned oil agents can be used alone or in combination of two or more types thereof, if necessary.

In the cosmetics of the present invention, as dispersants, emulsifiers, cleansers, or surface-treatment agents of other components, one or more surfactants selected from the group consisting of anionic surfactants, cationic surfactants, non-ionic surfactants, amphoteric surfactants and semi-polar surfactants can be used together. Hereinafter, they are described in detail.

As examples of anionic surfactants, mention may be made of saturated or unsaturated fatty acid salts such as sodium laurate, sodium stearate, sodium oleate, sodium linoleate and the like; alkylsulfuric acid salts; alkylbenzenesulfonic acids such as hexylbenzenesulfonic acid, octylbenzenesulfonic acid, dodecylbenzenesulfonic acid and the like, as well as salts thereof; polyoxyalkylene alkyl ether sulfuric acid salts; polyoxyalkylene alkenyl ether sulfuric acid salts; polyoxyethylene alkylsulfuric ester salts; sulfosuccinic acid alkyl ester salts; polyoxyalkylene sulfosuccinic acid alkyl ester salts; polyoxyalkylene alkylphenyl ether sulfuric acid salts; alkanesulfonic acid salts; octyltrimethylammonium hydroxide; dodecyltrimethylammonium hydroxide; alkyl sulfonates; polyoxyethylene alkylphenyl ether sulfuric acid salts; polyoxyalkylene alkyl ether acetic acid salts; alkyl phosphoric acid salts; polyoxyalkylene alkyl ether phosphoric acid salts; acylglutamic acid salts; α-acylsulfonic acid salts; alkylsulfonic acid salts; alkylallylsulfonic acid salts; α-olefinsulfonic acid salts; alkylnaphthalene sulfonic acid salts; alkanesulfonic acid salts; alkyl- or alkenylsulfuric acid salts; alkylamidesulfuric acid salts; alkyl- or alkenylphosphoric acid salts; alkylamidephosphoric acid salts; alkyloylalkyl taurine salts; N-acylamino acid salts; sufosuccinic acid salts; alkyl ether carboxylic acid salts; amide ether carboxylic acid salts; α-sulfofatty acid ester salts; alanine derivatives; glycine derivatives; and arginine derivatives. As examples of salts, mention may be made of alkali metal salts such as a sodium salt and the like, alkaline earth metal salts such as a magnesium salt and the like, alkanolamine salts such as a triethanolamine salt and the like, and an ammonium salt.

As examples of cationic surfactants, mention may be made of alkyltrimethylammonium chloride, stearyltrimethylammonium chloride, lauryltrimethylammonium chloride, cetyltrimethylammonium chloride, beef tallow alkyltrimethylammonium chloride, behenyltrimethylammonium chloride, stearyltrimethylammonium bromide, behenyltrimethylammonium bromide, distearyldimethylammonium chloride, dicocoyldimethylammonium chloride, dioctyldimethylammonium chloride, di(POE) oleylmethylammonium (2EO) chloride, benzalkonium chloride, alkyl benzalkonium chloride, alkyl dimethylbenzalkonium chloride, benzethonium chloride, stearyl dimethylbenzylammonium chloride, lanolin derivative quaternary ammonium salt, stearic acid diethylaminoethylamide, stearic dimethylaminopropylamide, behenic acid amide propyldimethylhydroxypropylammonium chloride, stearoyl colaminoformyl methylpyridinium chloride, cetylpyridinium chloride, tall oil alkylbenzyl hydroxyethylimidazolinium chloride, and benzylammonium salt.

As examples of nonionic surfactants, mention may be made of polyoxyalkylene ethers, polyoxyalkylene alkyl ethers, polyoxyalkylene fatty acid esters, polyoxyalkylene fatty acid diesters, polyoxyalkylene resin acid esters, polyoxyalkylene (hardened) castor oils, polyoxyalkylene alkyl phenols, polyoxyalkylene alkyl phenyl ethers, polyoxyalkylene phenyl phenyl ethers, polyoxyalkylene alkyl esters, polyoxyalkylene alkyl esters, sorbitan fatty acid esters, polyoxyalkylene sorbitan alkyl esters, polyoxyalkylene sorbitan fatty acid esters, polyoxyalkylene sorbitol fatty acid esters, polyoxyalkylene glycerol fatty acid esters, polyglycerol alkyl ethers, polyglycerol fatty acid esters, sucrose fatty acid esters, fatty acid alkanolamides, alkylglucosides, polyoxyalkylene fatty acid bisphenyl ethers, polypropylene glycol, diethylene glycol, polyoxyalkylene-modified silicones, polyglycerylmodified silicones, glyceryl-modified silicones, sugar-modified silicones, fluorine-based surfactants, polyoxyethylene/polyoxypropylene block polymers, and alkyl polyoxyethylene/polyoxypropylene block polymer ethers.

As examples of amphoteric surfactants, mention may be made of imidazoline-type, amidobetaine-type, alkylbetaine-type, alkylamidobetaine-type, alkylsulfobetaine-type, amidosulfobetaine-type, hydroxysulfobetaine-type, carbobetaine-type, phosphobetaine-type, aminocarboxylic acid-type, and amidoamino acid-type amphoteric surfactants. More particularly, as examples thereof, mention may be made of imidazoline-type amphoteric surfactants such as sodium 2-undecyl-N,N,N-(hydroxyethylcarboxymethyl)-2-imidazoline, 2-cocoyl-2-imidazolinium hydroxide-1-carboxyethyloxy disodium salt and the like; alkylbetaine-type amphoteric surfactants such as lauryl dimethylaminoacetic acid betaine, myristyl betaine and the like; and amidobetaine-type amphoteric surfactants such as coconut oil fatty acid amidopropyl dimethylamino acetic acid betaine, palm kernel oil fatty acid amidopropyl dimethylamino acetic acid betaine, beef tallow fatty acid amidopropyl dimethylamino acetic acid betaine, hardened beef tallow fatty acid amidopropyl dimethylamino acetic acid betaine, lauric amidopropyl dimethylamino acetic acid betaine, myristic amidopropyldimethylamino acetic acid betaine, palmitic amidopropyldimethylamino acetic acid betaine, stearic amidopropyl dimethylamino acetic acid betaine, oleic amidopropyl dimethylamino acetic acid betaine and the like; alkyl sulfobetaine-type amphoteric surfactants such as coconut oil fatty acid dimethyl sulfopropyl betaine and the like; alkylhydroxy sulfobetaine-type amphoteric surfactants such as lauryl dimethylaminohydroxy sulfobetaine and the like; phosphobetaine-type amphoteric surfactants such as laurylhydroxy phosphobetaine and the like; amidoamino acid-type amphoteric surfactants such as sodium N-lauroyl-N'-hydroxyethyl-N'-carboxymethyl ethylenediamine, sodium N-oleoyl-N'-hydroxyethyl-N'-carboxymethyl ethylenediamine, sodium N-cocoyl-N'-hydroxyethyl-N'-carboxymethyl ethylenediamine, potassium N-lauroyl-N'-hydroxyethyl-N'-carboxymethyl ethylenediamine, potassium N-oleoyl-N'-hydroxyethyl-N'-carboxymethyl ethylenediamine, sodium N-lauroyl-N-hydroxyethyl-N'-carboxymethyl ethylenediamine, sodium N-oleoyl-N-hydroxyethyl-N'-carboxymethyl ethylenediamine, sodium N-cocoyl-N-hydroxyethyl-N'-carboxymethyl ethylenediamine, monosodium N-lauroyl-N-hydroxyethyl-N',N'-dicarboxymethyl ethylenediamine, monosodium N-oleoyl-N-hydroxyethyl-N',N'-dicarboxymethyl ethylenediamine, monosodium N-cocoyl-N-hydroxyethyl-N',N'-dicarboxymethyl ethylenediamine, disodium N-lauroyl-N-hydroxyethyl-N',N'-dicarboxymethyl ethylenediamine, disodium N-oleoyl-N-hydroxyethyl-N',N'-dicarboxymethyl ethylenediamine, disodium N-cocoyl-N-hydroxyethyl-N',N'-dicarboxymethyl ethylenediamine and the like.

As examples of semi-polar surfactants, mention may be made of alkylamine oxide-type surfactants, alkylamine oxides, alkylamide amine oxides, alkylhydroxyamine oxides and the like. Alkyldimethylamine oxides having 10 to 18 carbon atoms, alkoxyethyl dihydroxyethylamine oxides having 8 to 18 carbon atoms and the like are preferably used. More particularly, as examples thereof, mention may be made of dodecyldimethylamine oxide, dimethyloctylamine oxide, diethyldecylamine oxide, bis-(2-hydroxyethyl) dodecylamine oxide, dipropyltetradecylamine oxide, methylethylhexadecylamine oxide, dodecylamidopropyldimethylamine oxide, cetyldimethylamine oxide, stearyldimethylamine oxide, tallow dimethylamine oxide, dimethyl-2-hydroxyoctadecylamine oxide, lauryldimethylamine oxide, myristyldimethylamine oxide, stearyldimethylamine oxide, isostearyldimethylamine oxide, coconut fatty acid alkyldimethylamine oxide, caprylic amide propyldimethylamine oxide, capric amide propyldimethylamine oxide, lauric amide propyldimethylamine oxide, myristic amide propyldimethylamine oxide, palmitic amide propyldimethylamine oxide, stearic amide propyldimethylamine oxide, isostearic amide propyldimethylamine oxide, oleic amide propyldimethylamine oxide, ricinoleic amide propyldimethylamine oxide, 12-hydroxystearic amide propyldimethylamine oxide, coconut fatty acid amide propyldimethylamine oxide, palm kernel oil fatty acid amide propyldimethylamine oxide, castor oil fatty acid amide propyldimethylamine oxide, lauric amide ethyldimethylamine oxide, myristic amide ethyldimethylamine oxide, coconut fatty acid amide ethyldimethylamine oxide, lauric amide ethyldiethylamine oxide, myristic amide ethyldiethylamine oxide, coconut fatty acid amide ethyldiethylamine oxide, lauric amide ethyldihydroxyethylamine oxide, myristic amide ethyldihydroxyethylamine oxide, and coconut fatty acid amide ethyldihydroxyethylamine oxide.

The cosmetics of the present invention can contain various cosmetic raw materials, in addition to the aforementioned components. The aforementioned raw materials are preferably hydrophobic so that they are not dissolved in water at all or have a solubility below 1% by weight with respect to 100 g of water. As examples of the aforementioned cosmetic raw materials, mention may be made of, for example, powder, coloring agents, water-soluble polymers, oil-soluble gelling agents, organo-modified clay minerals, silicone gums, silicone resins, organic resins such as silicone elastomers (in particular, powdery silicone elastomers), crosslinkable organopolysiloxanes, acryl silicone dendrimer copolymers, polyamide-modified silicones, waxy alkyl-modified silicones or alkyl-modified silicone resins, polyvinyl alcohols and the like, other organo-modified silicones, UV-ray protective components, bioactive components, perfumes and the like.

In addition, in the cosmetics of the present invention, components usually used in cosmetics can be blended within a range which does not impair the effects of the present invention, such as water, powder or coloring agents, alcohols, water-soluble polymers, film-forming agents, oil agents, oil-soluble gelling agents, organo-modified clay minerals, surfactants, resins, UV-ray absorbers, humectants, preservatives, antibacterial agents, perfumes, salts, antioxidants, pH adjustors, chelating agents, fresheners, anti-inflammatory agents, components for beautifying skin such as whitening agents, cell-activators, agents for ameliorating skin roughness, blood circulation promoters, astringents, antisebborrheic agents and the like, vitamins, amino acids, nucleic acids, hormones, clathration compounds, bioactive substances, and perfumes. The components are not particularly restricted thereto.

Hereinafter, the aforementioned other cosmetic raw materials are described.

As examples of powders and coloring agents, mention may be made of, for example, inorganic powders, organic powders, surfactant metal salt powders (metallic soaps), colored pigments, pearl pigments, metal powder pigments and the like. In addition, hybrid products of the aforementioned pigments can also be used. More particularly, as examples of inorganic powders, mention may be made of titanium oxide, zirconium oxide, zinc oxide, cerium oxide, magnesium oxide, barium sulfate, calcium sulfate, magnesium sulfate, calcium carbonate, magnesium carbonate, talc, mica, kaolin, sericite, white mica, synthetic mica, phlogopite, lepidolite, black mica, lithia mica, silicic acid, silicic acid anhydride, aluminum silicate, sodium silicate, magnesium sodium silicate, magnesium silicate, aluminum magnesium silicate, calcium silicate, barium silicate, strontium silicate, metal salts of tungstic acid, hydroxyapatite, vermiculite, higilite, bentonite, montmorillonite, hectorite, zeolite, ceramic powder, dicalcium phosphate, alumina, aluminum hydroxide, boron nitride, and the like. As examples of organic powders, mention may be made of polyamide powder, polyester powder, polyethylene powder, polypropylene powder, polystyrene powder, polyurethane powder, benzoguanamine powder, polymethylbenzoguanamine powder, polytetrafluoroethylene powder, poly(methyl methacrylate) powder, cellulose, silk powder, nylon powder, nylon 12, nylon 6, silicone powder, silicone gum powder, silicone elastomer spherical powder the surface of which is coated with polymethylsilsesquioxane, polymethylsilsesquioxane spherical powder, copolymers of styrene and acrylic acid, copolymers of divinylbenzene and styrene, vinyl resin, urea resin, phenol resin, fluorine resin, silicon resin, acrylic resin, melamine resin, epoxy resin, polycarbonate resin, microcrystalline fiber powder, starch powder, lauroyl lysine and the like. As examples of surfactant metal salt powders, mention may be made of zinc stearate, aluminum stearate, calcium stearate, magnesium stearate, zinc myristate, magnesium myristate, zinc palmitate, zinc laurate, zinc cetylphosphate, calcium cetylphosphate, sodium zinc cetylphosphate, and the like. As examples of colored pigments, mention may be made of inorganic red pigments such as red iron oxide, iron oxide, iron hydroxide, iron titanate and the like; inorganic brown pigments such as gamma-iron oxide and the like; inorganic yellow pigments such as yellow iron oxide, ocher, and the like; inorganic black iron pigments such as black iron oxide, carbon black and the like; inorganic purple pigments such as manganese violet, cobalt violet, and the like; inorganic green pigments such as chromium hydroxide, chromium oxide, cobalt oxide, cobalt titanate, and the like; inorganic blue pigments such as Prussian blue, ultramarine blue, and the like; laked pigments of tar pigments such as Red No. 3, Red No. 104, Red No. 106, Red No. 201, Red No. 202, Red No. 204, Red No. 205, Red No. 220, Red No. 226, Red No. 227, Red No. 228, Red No. 230, Red No. 401, Red No. 505, Yellow No. 4, Yellow No. 5, Yellow No. 202, Yellow No. 203, Yellow No. 204, Yellow No. 401, Blue No. 1, Blue No. 2, Blue No. 201, Blue No. 404, Green No. 3, Green No. 201, Green No. 204, Green No. 205, Orange No. 201, Orange No. 203, Orange No. 204, Orange No. 206, Orange No. 207 and the like, laked pigments of natural pigments such as carminic acid, laccaic acid, carthamin, brazilin, crocin and the like. As examples of pearl pigments, mention may be made of titanium oxide-coated mica, titanium mica, iron oxide-coated titanium mica, titanium oxide-coated mica, bismuth oxychloride, titanium oxide-coated bismuth oxychloride, titanium oxide-coated talc, fish scale foil, titanium oxide-coated colored mica, and the like. As examples of metal powder pigments, mention may be made of powders of metals such as aluminum, gold, silver, copper, platinum, stainless steel, and the like.

In addition, as examples thereof, mention may also be made of powders absorbing or scattering ultraviolet rays such as fine particulate titanium oxide, fine particulate iron-containing titanium oxide, fine particulate zinc oxide, fine particulate cerium oxide and composite products thereof.

In addition, in the aforementioned powders and/or coloring agents, a part or all parts thereof are, in particular, preferably subjected to a water-repellent treatment. In addition, composited products in which the aforementioned powders and/or coloring agents are mutually composited or surface-treated products in which the aforementioned powders and/or coloring agents are subjected to a surface treatment with a general oil agent, a silicone compound other than the organopolysiloxane of the present invention, a fluorine compound, a surfactant or the like can also be used. One type thereof or two or more types thereof can be used, if necessary. The blending amount of the aforementioned powders and/or coloring agents preferably ranges from 0.1 to 99% by weight with respect to the total amount of the cosmetic. In particular, in the case of a powdery solid cosmetic, the blending amount of the aforementioned powders and/or coloring agents preferably ranges from 80 to 99% by weight with respect to the total amount of the cosmetic.

As examples of other water-repellant treatments, mention may be made of treatments in which the aforementioned powders and/or coloring agents are treated with various water-repellent surface treatment agents, such as organosiloxane treatments such as a methylhydrogenpolysiloxane treatment, a silicone resin treatment, a silicone gum treatment, an acryl silicone treatment, a fluorinated silicone treatment and the like; metallic soap treatments such as a zinc stearate treatment and the like; silane treatments such as a silane coupling agent treatment, an alkylsilane treatment and the like; fluorine compound treatments such as a perfluoroalkylsilane treatment, a perfluoroalkyl phosphate treatment, a perfluoro polyether treatment and the like; amino acid treatments such as an N-lauroyl-L-lysine treatment and the like; oil agent treatments such as a squalane treatment and the like; acryl treatments such as an alkyl acrylate treatment and the like. The aforementioned treatments can be used in combination of one or more types thereof.

As the water-soluble polymers, one type or two or more types thereof can be used. As examples of natural water-soluble polymers, mention may be made of vegetable-based polymers such as gum Arabic, tragacanth gum, galactan, guar gum, carob gum, Karaya gum, carrageenan, pectin, agar, quince seed, algal colloide, starch (rice, corn, potato, or wheat), glycyrrhizinic acid and the like; microorganism-based polymers such as xanthan gum, dextran, succinoglucan, pullulan, and the like; and animal-based polymers such as collagen, casein, albumin, gelatin, and the like. In addition, as examples of semi-synthetic water-soluble polymers, mention may be made of, for example, starch-based polymers such as carboxymethyl starch, methyhydroxypropyl starch, and the like; cellulose-based polymers such as methylcellulose, nitrocellulose, ethylcellulose, methylhydroxypropylcellulose, hydroxyethylcellulose, sodium cellulose sulfate, hydroxypropylcellulose, sodium carboxymethylcellulose (CMC), crystalline cellulose, cellulose powder, and the like; and alginate-based polymers such as sodium alginate, propylene glycol alginate and the like. As examples of synthetic water-soluble polymers, mention may be made of, for example, vinyl-based polymers such as polyvinyl alcohol, polyvinyl methyl ether-based polymer, polyvinylpyrrolidone, carboxyvinyl polymer (CARBOPOL 940, 941; manufactured by BF Goodrich Corporation); polyoxyethylene-based polymers such as polyethylene glycol 20,000, polyethylene glycol 6,000, polyethylene glycol 4,000 and the like; copolymer-based polymers such as a copolymer of polyoxyethylene and polyoxypropylene, PEG/PPG methyl ether and the like; acryl-based polymers such as poly(sodium acrylate), poly(ethyl acrylate), polyacrylamide and the like; polyethylene imines; cationic polymers and the like. As examples of other cationic water-soluble polymers, in particular, as components which are preferably blended in hair cosmetics, quaternary nitrogen-modified polysaccharides such as cation-modified cellulose, cation-modified hydroxyethylcellulose, cation-modified guar gum, cation-modified locust bean gum, cation-modified starch and the like; dimethyldiallylammonium chloride derivatives such as a copolymer of dimethyldiallylammonium chloride and acrylamide, poly(dimethylmethylene piperidinium chloride) and the like; and vinylpyrrolidone derivatives such as a salt of a copolymer of vinylpyrrolidone and dimethylaminoethyl methacrylic acid, a copolymer of vinylpyrrolidone and methacrylamide propyltrimethylammonium chloride, a copolymer of vinylpyrrolidone and methylvinylimidazolium chloride and the like.

As examples of oil-soluble gelling agents, mention may be made of metallic soaps such as aluminum stearate, magnesium stearate, zinc myristate and the like; amino acid derivatives such as N-lauroyl-L-glutamic acid, α,γ-di-n-butylamine and the like; dextrin fatty acid esters such as dextrin palmitate, dextrin stearate, dextrin 2-ethylhexanoate palmitate and the like; sucrose fatty acid esters such as sucrose palmitate, sucrose stearate and the like; benzylidene derivatives of sorbitol such as monobenzylidene sorbitol, dibenzylidene sorbitol and the like; and the like. The oil-soluble gelling agents can be used alone or in combination of two or more types thereof, if necessary.

As examples of organo-modified clay minerals, mention may be made of, for example, dimethylbenzyldodecylammonium montmorillonite clay, dimethyldioctadecylammonium montmorillonite clay, dimethylalkylammonium hectorite, benzyldimethylstearylammonium hectorite, distearyldimethylammonium chloride-treated aluminum magnesium cinnamate and the like. As examples of commercially available products thereof, mention may be made of Benton 27 (benzyldimethylstearylammonium chloride-treated hectorite, manufactured by Nationalred Co.), Benton 38 (distearyldimethylammonium chloride-treated hectorite, manufactured by Nationalred Co.) and the like.

The silicone gum is a linear diorganopolysiloxane having an ultra-high degree of polymerization, and is also referred to as a silicone raw rubber or an organopolysiloxane gum. As representative examples thereof, there are those represented by the following general formula:

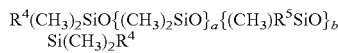

wherein $R^5$ is a group selected from a vinyl group, a phenyl group, an alkyl group having 6 to 20 carbon atoms, an aminoalkyl group having 3 to 15 carbon atoms, a perfluoroalkyl group having 3 to 15 carbon atoms, and a quaternary ammonium base-containing alkyl group having 3 to 15 carbon atoms; the terminal $R^4$ is a group selected from an alkyl group having 1 to 8 carbon atoms, a phenyl group, a vinyl group, an aminoalkyl group having 3 to 15 carbon atoms, a hydroxyl group and an alkoxy group having 1 to 8 carbon atoms; a=2,000 to 6,000; b=0 to 1,000; and a+b=2,000 to 6,000.

The silicone resin is an organopolysiloxane with a highly branched molecular structure, a net-like molecular structure or a cage-like molecular structure, and may be in the form of a liquid or solid at room temperature. Any silicone resins usually used in cosmetics can be used unless they are contrary to the purposes of the present invention. As examples of the solid silicone resins, mention may be made of, for example, MQ resins, MDQ resins, MTQ resins, MDTQ resins, TD resins, TQ resins, or TDQ resins comprising any combinations of a triorganosiloxy unit (M unit) (wherein the organo group is a methyl group alone, or a methyl group in combination with a vinyl group or a phenyl group), a diorganosiloxy unit (D unit) (wherein the organo group is a methyl group alone, or a methyl group in combination with vinyl group or phenyl group), a monoorganosiloxy unit (T unit) (wherein the organo group is a methyl group, a vinyl group or a phenyl group), and a siloxy unit (Q unit). In addition, as other examples thereof, mention may be made of trimethylsiloxysilicic acid, polyalkylsiloxysilicic acid, trimethylsiloxysilicic acid containing dimethylsiloxy units and alkyl(perfluoroalkyl) siloxysilicic acid. The aforementioned silicone resins are preferably oil soluble, and, in particular, preferably are soluble in D4 or D5.

A silicone elastomer in any form can be blended in the cosmetic in accordance with the purpose thereof. In particular, the silicone elastomer is preferably blended as organopolysiloxane elastomer spherical powders or a crosslinking organopolysiloxane.

The silicone elastomer is mainly a crosslinked product of a linear diorganopolysiloxane, and can be in various forms such as a spherical form, a flat form, an amorphous form and the like. The elastomer may be in the form of an oil dispersant without shapes. In the cosmetic of the present invention, silicone elastomer powders in the form of particles are preferred, which have a primary particle size observed by an electronic microscope and/or an average primary particle size measured by a laser diffraction/scattering method ranging from 0.1 to 50 μm, and in which the primary particle is in the spherical form. In addition, the silicone elastomer constituting the silicone elastomer powder may have a hardness preferably not exceeding 80, and more preferably not exceeding 65, when measured by means of a type A durometer according to JIS K 6253 "Method for determining hardness of vulcanized rubber or thermoplastic rubber".

As examples of the aforementioned silicone elastomer powders, mention may be made of, for example, those described in Japanese Unexamined Patent Application, First Publication No. H02-243612; Japanese Unexamined Patent Application, First Publication No. H08-12545; Japanese Unexamined Patent Application, First Publication No. H08-12546; Japanese Unexamined Patent Application, First Publication No. H08-12524; Japanese Unexamined Patent Application, First Publication No. H09-241511; Japanese Unexamined Patent Application, First Publication No. H10-36219; Japanese Unexamined Patent Application, First Publication No. H11-193331; Japanese Unexamined Patent Application, First Publication No. 2000-281523 and the like. As commercially available products, there are Trefil E-505, Trefil E-506, Trefil E-507, and Trefil E-508 of the Trefil E series, manufactured by Dow Corning Toray Co., Ltd., and the like, and crosslinking silicone powders listed in "Japanese Cosmetic Ingredients Codex (JCIC)" correspond thereto. The aforementioned silicone elastomer powders may be subjected to a surface treatment. As examples of the surface treatment agents, mention may be made of methylhydrogenpolysiloxane, silicone resins, metallic soap, silane coupling agents, silica, inorganic oxides such as titanium oxide and the like and fluorine compounds such as perfluoroalkylsilane, perfluoroalkyl phosphoric ester salts and the like.

The silicone elastomer powders are preferably blended in cosmetics in the form of a paste product which is a product kneaded with oil agents or an aqueous dispersion. More particularly, as examples thereof, mention may be made of paste products prepared by kneading silicone elastomer powders and oil components which are liquid at room temperature, and selected from the group consisting of ester oils, hydrocarbon oils, higher alcohols, vegetable oils and animal oils; and dispersions in which the silicone elastomer powders are dispersed in water containing an emulsifier by means of mechanical power. Among the raw materials for cosmetics in which silicone elastomer powders are dispersed in a medium, as examples of those preferably used in the present invention, mention may be made of commercially available products such as "BY29-129" and "PF-2001 PIF Emulsion" manufactured by Dow Corning Toray Silicone Co., Ltd., and the like.

By blending an aqueous dispersion (=suspension) of the aforementioned silicone elastomer powders, the sensation during use of the cosmetics of the present invention can be further improved, and in this point of view, the silicone elastomer powders are extremely useful.

As the crosslinking organopolysiloxanes, non-emulsifiable organopolysiloxanes without hydrophilic parts such as polyoxyalkylene units which have a three-dimensional crosslinked structure by a reaction between the organopolysiloxane chains and the crosslinking components and the like are preferred. The aforementioned crosslinking organopolysiloxanes can be used without restrictions of physical modes and preparation methods such as dilution, properties and the like. As particularly preferable examples thereof, mention may be made of α, ω-diene crosslinking silicone elastomers (as commercially available products, DC 9040 Silicone Elastomer Blend, DC 9041 Silicone Elastomer Blend, DC 9045 Silicone Elastomer Blend, and DC 9046 Silicone Elastomer Blend, manufactured by Dow Corning Corporation in the USA) described in U.S. Pat. No. 5,654,362.

Acryl silicone dendrimer copolymers can be used in accordance with the purposes in the cosmetics of the present invention. As examples thereof, mention may be, in particular, preferably made of vinyl polymers having a carbosiloxane dendrimer structure at the side chain described in Japanese Patent No. 4,009,382 (Japanese Unexamined Patent Application, First Publication No. 2000-063225). As examples of commercially available products, mention may be made of FA 4001 CM Silicone Acrylate, and FA 4002 ID Silicone Acrylate, manufactured by Dow Corning Toray Co., Ltd., and the like.

Polyamide-modified silicones used in accordance with the purposes can be blended in the cosmetics of the present invention. As examples thereof, mention may be made of, for example, siloxane-based polyamides described in U.S. Pat. No. 5,981,680, and as examples of commercially available products, mention may be made of 2-8178 Gellant, 2-8179 Gellant and the like (manufactured by Dow Corning Corporation, in the USA).

The alkyl-modified silicone waxes used in accordance with the purposes can be blended in the cosmetics of the present invention. The aforementioned alkyl-modified silicone wax may be an alkyl-modified silicone in the form of a wax at room temperature. As examples thereof, mention may be made of a methyl(long chain alkyl)polysiloxane having both molecular terminals capped with trimethylsiloxy groups, a copolymer of a dimethylpolysiloxane having both molecular terminals capped with trimethylsiloxy groups and a methyl(long chain alkyl)siloxane, a both terminal (long chain alkyl)-modified dimethylpolysiloxane and the like. As examples of commercially available products thereof, mention may be made of, AMS-C30 Cosmetic Wax, 2503 Cosmetic Wax and the like (manufactured by Dow Corning Corporation, in the USA).

As examples of alkyl-modified silicone resin waxes used in accordance with the purposes of the cosmetics of the present invention, mention may be preferably made of, for example, silsesquioxane resin described in Published Japanese Translation No. 2007-532754 of the PCT International Application.

As examples of organic resins used in accordance with the purposes of the cosmetics of the present invention, mention may be made of polyvinyl alcohols, polyvinylpyrrolidones, poly(alkyl acrylate) copolymers and the like.

The organo-modified silicones other than those described above are, in particular, preferably lipophilic. As examples thereof, mention may be made of amino-modified silicones, amino polyether-modified silicones, epoxy-modified silicones, carboxyl-modified silicones, amino acid-modified silicones, carbinol-modified silicones, acryl-modified silicones, phenol-modified silicones, amidoalkyl-modified silicones, aminoglycol-modified silicones, and alkoxy-modified silicones. The aforementioned organo-modified silicones may have an alkylene chain, an aminoalkylene chain or a polyether chain, in addition to the polysiloxane bonds as a main chain, with a degree such that the compound does not exhibit hydrophilic properties, and the organo-modified group may exist at the side chain or at one terminal or both terminals of the polysiloxane chain. In the case of using the cosmetics of the present invention as hair cosmetics, amino-modified silicones, carbinol-modified silicones, amino polyether-modified silicones, or amino glycol-modified silicones can be preferably used. As general examples thereof, amino-modified silicones having a 3-aminopropyl group, an N-(2-aminoethyl)-3-aminopropyl group and the like can be mentioned.

Among UV-ray protective components, there are inorganic UV-ray protective components and organic UV-ray protective components. If the cosmetics of the present invention are sunscreen cosmetics, at least one type of inorganic or organic UV-ray protective component, and in particular, an organic UV-ray protective component is preferably contained.

The inorganic UV-ray protective components may be components in which the aforementioned inorganic powder pigments, metal powder pigments and the like are blended as UV-ray dispersants. As examples thereof, mention may be made of metal oxides such as titanium oxide, zinc oxide, cerium oxide, titanium suboxide, iron-doped titanium oxides and the like; metal hydroxides such as iron hydroxides and the like; metal flakes such as platy iron oxide, aluminum flake and the like; and ceramics such as silicon carbide and the like. Among these, at least one type of a material selected from fine particulate metal oxides or fine particulate metal hydroxides with an average particle size ranging from 1 to 100 nm in the form of granules, plates, needles, or fibers is, in particular, preferred. The aforementioned powders are preferably subjected to conventional surface treatments such as fluorine compound treatments, among which a perfluoroalkyl phosphate treatment, a perfluoroalkylsilane treatment, a perfluoropolyether treatment, a fluorosilicone treatment, and a fluorinated silicone resin treatment are preferred; silicone treatments, among which a methylhydrogenpolysiloxane treatment, a dimethylpolysiloxane treatment, and a vapor-phase tetramethyltetrahydrogencyclotetrasiloxane treatment are preferred; silicone resin treatments, among which a trimethylsiloxysilicic acid treatment is preferred; pendant treatments which are methods of adding alkyl chains after the vapor-phase silicone treatment; silane coupling agent treatments; titanium coupling agent treatments; silane treatments among which an alkylsilane treatment and an alkylsilazane treatment are preferred; oil agent treatments; N-acylated lysine treatments; polyacrylic acid treatments; metallic soap treatments in which a stearic acid salt or a myristic acid salt is preferably used; acrylic resin treatments; metal oxide treatments and the like. A plurality of the treatments described above are preferably carried out. For example, the surface of the fine particulate titanium oxide is coated with a metal oxide such as silicon oxide, alumina or the like, and then, a surface treatment with an alkylsilane is carried out. The total amount of the material used for the surface treatment preferably ranges from 0.1 to 50% by weight based on the amount of the powder.

The organic UV-ray protective components are lipophilic UV-ray protective components, and one type or two or more types of the organic UV-ray protective components can be used. As examples thereof, mention may be made of, for example, benzoic acid-based UV-ray absorbers such as paraaminobenzoic acid and the like, anthranilic acid-based UV-ray absorbers such as methyl anthranilate and the like, cinnamic acid-based UV-ray absorbers such as octyl paramethoxycinnamate and the like, benzophenone-based UV-ray absorbers such as 2,4-dihydroxybenzophenone and the like, urocanic acid-based UV-ray absorbers such as ethyl urocanate and the like, dibenzoylmethane-based UV-ray absorbers such as 4-t-butyl-4'-methoxydibenzoylmethane and the like, and the like.

More particularly, as examples of the aforementioned organic UV-ray protective components, mention may be made of benzoic acid-based UV-ray absorbers such as paraaminobenzoic acid (hereinafter, referred to as PABA), PABA monoglycerol ester, N,N-dipropoxy-PABA ethyl ester, N,N-diethoxy-PABA ethyl ester, N,N-dimethyl-PABA ethyl ester, N,N-dimethyl-PABA butyl ester and the like; anthranilic acid-based UV-ray absorbers such as homomenthyl N-acetylanthranilate and the like; salicylic acid-based UV-ray absorbers such as amyl salicylate, menthyl salicylate, homomenthyl salicylate, octyl salicylate, phenyl salicylate, benzyl salicylate, p-isopropanolphenyl salicylate and the like; cinnamic acid-based UV-ray absorbers such as octyl cinnamate, ethyl 4-isopropylcinnamate, methyl 2,5-diisopropylcinnamate, ethyl 2,4-diisopropylcinnamate, methyl 2,4-diisopropylcinnamate, propyl p-methoxycinnamate, isopropyl p-methoxycinnamate, isoamyl p-methoxycinnamate, octyl p-methoxycinnamate (2-ethylhexyl p-methoxycinnamate), 2-ethoxyethyl p-methoxycinnamate, cyclohexyl p-methoxy cinnamate, ethyl α-cyano-β-phenylcinnamate, 2-ethylhexyl α-cyano-β-phenylcinnamate, glyceryl mono-2-ethylhexanoyl-diparamethoxycinnamate, 3-methyl 4-[methylbis(trimethylsiloxy)silyl]butyl 3,4,5-trimethoxycinnamate and the like; benzophenone-based UV-ray absorbers such as 2,4-dihydroxybenzophenone, 2,2'-dihydroxy-4-methoxybenzophenone, 2,2'-dihydroxy-4,4'-dimethoxybenzophenone, 2,2',4,4'-tetrahydroxybenzophenone, 2-hydroxy-4-methoxybenzophenone, 2-hydroxy-4-methoxy-4'-methylbenzophenone, 2-hydroxy-4-methoxybenzophenone 5-sulfonate, 4-phenylbenzophenone, 2-ethylhexyl-4'-phenylbenzophenone 2-carboxylate, hydroxy-4-n-octoxybenzophenone, 4-hydroxy-3-carboxybenzophenone and the like; 3-(4'-methylbenzylidene)-d,1-camphor; 3-benzylidene-d,1-camphor; urocanic acid; ethyl urocanate; 2-phenyl-5-methylbenzoxazole; 2,2'-hydroxy-5-methylphenyl benzotriazole; 2-(2'-hydroxy-5'-t-octylphenyl)benzotriazole; 2-(2'-hydroxy-5'-methylphenyl)benzotriazole; dibenzaladine; dianisoylmethane; 4-methoxy-4'-t-butylbenzoylmethane 5-(3,3-dimethyl-2-norbonylidene)-3-pentan-2-one and the like.

Furthermore, hydrophobic polymer powders containing the aforementioned organic UV-ray protective components inside thereof can also be used. The polymer powder may be hollow or not, may have an average primary particle size thereof ranging from 0.1 to 50 μm and may have a particle size distribution thereof of either broad or sharp. As examples of the polymers, mention may be made of acrylic resins, methacrylic resins, styrene resins, polyurethane resins, polyethylene, polypropylene, polyethylene terephthalate, silicone resins, nylons, acrylamide resins, and silylated polypeptide resins. Polymer powders containing the organic UV-ray protective components in the amount ranging from 0.1 to 30% by weight with respect to the amount of the powder are preferred. Polymer powders containing 4-tert-butyl-4'-methoxydibenzoylmethane, which is a UV-A absorber, are particularly preferred.

The UV-ray protective components which can be preferably used in the cosmetics of the present invention are at least one type of compound selected from the group consisting of fine particulate titanium oxide, fine particulate zinc oxide, 2-ethylhexyl paramethoxycinnamate, 4-tert-butyl-4'-methoxydibenzoylmethane, and benzophenone-based UV-ray absorbers. The aforementioned UV-ray protective components are commonly used and easily available, and exhibit superior effects of preventing ultraviolet rays. For these reasons, the aforementioned UV-ray protective components are preferably used. In particular, inorganic UV-ray protective components and organic UV-ray protective components are preferably used in combination. In addition, UV-A protective components and UV-B protective components are further preferably used in combination.

In the cosmetics of the present invention, other components usually used in cosmetics can be blended within a range which does not impair the effects of the present invention, such as alcohols, anti-microbial preservatives, physiologically active components, components for beautifying the skin (such as whitening agents, cell activators, agents for ameliorating skin roughness, blood circulation accelerators, astringents, antiseborrheic agents and the like), solvents, antioxidants, humectants, perfumes, salts, pH adjustors, chelating agents, algefacients, anti-inflammatory agents, vitamins, amino acids, nucleic acids, hormones, clathrate compounds and the like. They are not particularly restricted thereto.

As the alcohols, one type or two or more types of polyhydric alcohols and/or lower monovalent alcohols can be used. As examples of lower alcohols, mention may be made of ethanol, isopropanol, n-propanol, t-butanol, s-butanol and the like. As examples of polyhydric alcohols, mention may be made of divalent alcohols such as 1,3-butylene glycol, 1,2-butylene glycol, propylene glycol, trimethylene glycol, tetramethylene glycol, 2,3-butylene glycol, pentamethylene glycol, 2-butene-1,4-diol, dibutylene glycol, pentyl glycol, hexylene glycol, octylene glycol and the like; trivalent alcohols such as glycerol, trimethylolpropane, 1,2,6-hexanetriol and the like; polyhydric alcohols having tetra- or more valences such as pentaerythritol, xylitol and the like; sugar alcohols such as sorbitol, mannitol, maltitol, maltotriose, sucrose, erytritol, glucose, fructose, starch decomposed products, maltose, xylitose, starch decomposed reduction alcohols and the like. In addition to the aforementioned polyhydric alcohols having a low molecular weight, mention may be made of polyhydric alcohol polymers such as diethylene glycol, dipropylene glycol, triethylene glycol, polypropylene glycol, tetraethylene glycol, diglycerol, polyethylene glycol, triglycerol, tetraglycerol, polyglycerol and the like. Among these, 1,3-butylene glycol, sorbitol, dipropylene glycol, glycerol, and polyethylene glycol are, in particular, preferred. The blending amount thereof preferably ranges from 0.1 to 50% by weight with respect to the total amount of the cosmetic.

As examples of the antimicrobial preservatives blended in the cosmetics of the present invention depending on the purposes thereof, mention may be made of, for example, alkyl paraoxybenzoates, benzoic acid, sodium benzoate, sorbic acid, potassium sorbate, phenoxyethanol and the like. As examples of the antimicrobial agents, mention may be made of benzoic acid, salicylic acid, carbolic acid, sorbic acid, alkyl paraoxybenzoates, parachloromethacresol, hexachlorophene, benzalkonium chloride, chlorhexidine chloride, trichlorocarbanilide, trichlosan, photosensitizers and the like. In the case of lipsticks, the aforementioned compounds are not preferably contained.

As the biologically active components blended in the cosmetics of the present invention in accordance with the purposes thereof, mention may be made of substances imparting physiological activities to the skin when applied to the skin. As examples thereof, mention may be made of, for example, anti-inflammatory agents, anti-aging agents, UV-ray protective agents, astringents, antioxidants, hair-growing agents, hair tonic agents, humectants, blood circulation accelerators, antimicrobial agents, fungicides, desiccants, cold sensation agents, hot sensation agents, vitamins, amino acids, wound healing accelerators, irritation reducers, analgesics, cell activators, enzymatic ingredients, and the like. Among these, natural vegetable extract components, seaweed extract components and herbal medicine components are particularly preferred. In the present invention, one type or two or more types of the aforementioned physiologically active components are preferably blended.

As detailed examples thereof, mention may be made of, for example, *Angelica keiskei* extract, avocado extract, *Hydrangea serrata* extract, *Althaea officinalis* extract, *Arnica montana* extract, aloe extract, apricot extract, apricot kernel extract, *Gingko biloba* extract, fennel fruit extract, turmeric root extract, oolong tea extract, *Rosa multiflora* extract, *Echinacea angustifolia* leaf extract, *Scutellaria baicalensis* root Extract, *Phellodendron amurense* bark extract, *Coptis rhizome* extract, *Hordeum vulgare* seed extract, *Hypericum perforatum* extract, *Lamium album* extract, *Nasturtium officinale* extract, orange extract, dried sea water solution, seaweed extract, hydrolyzed elastin, hydrolyzed wheat powders, hydrolyzed silk, *Chamomilla recutita* extract, carrot extract, *Artemisia capillaris* flower extract, *Glycyrrhiza glabra* extract, *Hibiscus sabdariffa* extract, *Pyracantha fortuneana* extract, kiwi extract, *Cinchona succirubra* extract, cucumber extract, guanosine, *Gardenia florida* extact, *Sasa veitchii* extract, *Sophora angustifolia* extract, walnut extract, grapefruit extract, *Clematis vitalba* leaf extract, chlorella extract, *Morus alba* extract, *Gentiana lutea* extract, black tea extract, yeast extract, burdock extract, fermented rice bran extract, rice germ oil, *Symphytum officinale* leaf extract, collagen, *Vaccinum vitis* idaea extract, *Asiasarum sieboldi* extract, *Bupleurum falcatum* extract, umbilical extract, *Salvia* extract, *Crocus sativus* flower extract, sasa bamboo grass extract, *Crataegus cuneata* fruit extract, *Zanthoxylum piperitum* extract, *Corthellus shiitake* extract, *Rehmannia chinensis* root extract, *Lithospermum erythrorhizone* root extract, *Perilla ocymoides* extract, *Tilia cordata* extract, *Spiraea ulmaria* extract, *Paeonia albiflora* extract, *Acorns calamus* root extract, *Betula alba* extract, *Equisetum arvense* extract, *Hedera helix* extract, *Crataegus oxyacantha* extract, *Sambucus nigra* extract, *Achillea millefolium* extract, *Mentha piperita* leaf extract, sage extract, *Malva sylvestris* extract, *Cnidium officinale* root extract, *Swertia japonica* extract, soybean seed extract, *Zizyphus jujuba* fruit extract, thyme extract, *Camellia sinensis* leaf extract, *Eugenia caryophyllus* flower extract, *Imperata cylindrica* extract, *Citrus unshiu* peel extract, *Angelica acutiloba* root extract, *Calendula officinalis* extract, *Prunus persica* kernel extract, *Citrus aurantium* peel extract, *Houttuynia cordata* extract, tomato extract, natto extract, carrot extract, garlic extract, *Rosa canina* fruit extract, hibiscus extract, *Ophiopogon japonicus* root extract, *Nelumbo nucifera* extract, parsley extract, honey, *Hamamelis virginiana* extract, *Parietaria officinalis* extract, *Isodon trichocarpus* extract, bisabolol, *Eriobotrya japonica* extract, *Tussilago farfara* flower extract, *Petasites japonicus* extract, *Poria cocos* extract, *Ruscus aculeatus* root extract, grape extract, propolis, *Luffa cylindrica* fruit extract, safflower flower extract, peppermint extract, *Tillia miquellana* extract, *Paeonia suffruticosa* root extract, *Humulus lupulus* extract, *Pinus sylvestris* cone extract, horse chestnut extract, *Lysichiton camtschatcense* extract, *Sapindus mukurossi* peel extract, *Melissa officinalis* leaf extract, peach extract, *Centaurea cyanus* flower extract, *Eucalyptus globulus* leaf extract, *Saxifraga sarementosa* extract, *Citrus junos* extract, *Coix lacryma-jobi* seed extract, *Artemisia princeps* extract, lavender extract, apple extract, lettuce extract, lemon extract, *Astragalus sinicus* extract, rose extract, rosemary extract, *Roman chamomile* extract, and royal jelly extract.

In addition, as examples of the biologically active components, mention may be made of biological polymers such as deoxyribonucleic acid, mucopolysaccharides, sodium hyaluronate, sodium chondroitin sulfate, collagen, elastin, chitin, chitosan, hydrolyzed eggshell membrane and the like; amino acids such as glycine, valine, leucine, isoleucine, serine, threonine, phenylalanine, arginine, lysine, aspartic acid, glutamate, cystine, cysteine, methionine, tryptophan and the like; hormones such as estradiol, ethenyl estradiol and the like; oil-based ingredients such as sphingolipids, ceramides, cholesterol derivatives, phospholipids and the like; anti-inflammatory agents such as $\epsilon$-aminocaproic acid, glycyrrhizinic acid, lysozyme chloride, guaiazulene, hydrocortisone, allantoin, tranexamic acid, azulene and the like; vitamins such as vitamins A, B2, B6, C, D, and E, calcium pantothenate, biotin, nicotinic-acid amide, vitamin C ester, and the like; active ingredients such as allantoin, diisopropylamine dichloroacetate, 4-aminomethyl cyclohexanecarboxylic acid and the like; antioxidants such as carotinoids, flavonoids, tannins, lignans, saponins, butylated hydroxyanisole, dibutylhydroxytoluene, phytic acid and the like; cell activators such as $\alpha$-hydroxy acids, $\beta$-hydroxy acids, and the like; blood circulation accelerators such as $\gamma$-orizanol, vitamin E derivatives, and the like; wound healing agents such as retinol, retinol derivatives, and the like; algefacient agents such as cepharanthin, *Glycyrrhiza glabra* extract, cayenne tincture, hinokitiol, iodized garlic extract, pyridoxine hydrochloride, dl-$\alpha$-tocopherol, dl-$\alpha$-tocopherol acetate, nicotinic acid, nicotinic acid derivatives, calcium pantothenate, D-pantothenyl alcohol, acetyl pantothenyl ethyl ether, allantoin, isopropyl methyl phenol, capronium chloride, benzalkonium chloride, diphenhydramine hydrochloride, Takanal™, camphor, nonylic acid vanillylamide, nonanoic acid vanillylamide, piroctone olamine, glyceryl pentadecanoate, 1-menthol, camphor and the like; hair growing agents such as mononitroguaiacol, resorcin, $\gamma$-aminobutyric acid, benzethonium chloride, mexiletine hydrochloride, auxin, female hormones, cantharis tincture, cyclosporine, zinc pyrithione, hydrocortisone, minoxidil, polyoxyethylene sorbitan monostearate, peppermint oil, sasanishiki extract and the like; and the like.

As examples of skin-beautifying components, mention may be made of whitening agents such as placenta extracts, arbutin, glutathione, saxifrageous extracts and the like; cell activators such as royal jelly, and the like; agents for ameliorating skin roughness; blood circulation accelerators such as nonylic acid vanillylamide, benzyl nicotinate, beta-butoxyethyl nicotinate, capsaicin, gingerone, cantharide tincture, ichthammol, caffeine, tannic acid, alpha-borneol, tocopherol nicotinate, inositol hexanicotinate, cyclandelate, cinnarizine, tolazoline, acetylcholine, verapamil, cepharanthine, gamma-orizanol and the like; astringents such as zinc oxide, tannic acid and the like; antiseborrheic agents such as sulfur, thianthol and the like; and the like. As examples of vitamins, mention may be made of vitamin As such as vitamin A oil, retinol, retinol acetate, retinol palmitate and the like; vitamin Bs such as vitamin B2s such as riboflavin, riboflavin butyrate, flavin adenine dinucleotide and the like; vitamin B6s such as pyridoxine hydrochloride, pyridoxine dioctanoate, pyridoxine tripalmitate and the like; vitamin B12 and derivatives thereof; vitamin B15 and derivatives thereof, and the like; vitamin Cs such as L-ascorbic acid, L-ascorbyl dipalmitic acid esters, sodium L-ascorbyl 2-sulfate, dipotassium L-ascorbyl phosphoric acid diesters and the like; vitamin Ds such as ergocalciferol, cholecalciferol and the like; vitamin Es such as alpha-tocopherol, beta-tocopherol, gamma-tocopherol, dl-alpha-tocopherol acetate, dl-alpha-tocopherol nicotinate, dl-alpha-tocopherol succinate and the like; vitamin H; vitamin P; nicotinic acids such as nicotinic acid, benzyl nicotinate and the like; pantothenic acids such as calcium pantothenate, D-pantothenyl alcohol, pantothenyl ethyl ether, acetyl pantothenyl ethyl ether and the like; and the like.

As examples of pH adjustors blended in the cosmetics of the present invention depending on the purposes thereof, mention may be made of, for example, lactic acid, citric acid, glycolic acid, succinic acid, tartaric acid, dl-malic acid, potassium carbonate, sodium hydrogencarbonate, ammonium hydrogencarbonate and the like.

As examples of solvents blended in the cosmetics of the present invention depending on the purposes thereof, mention may be made of, for example, light isoparaffins, ethers, LPG, N-methylpyrrolidone, next-generation chlorofluorocarbons, and the like, in addition to water such as purified water, mineral water and the like.

As examples of antioxidants blended in the cosmetics of the present invention depending on the purposes thereof, mention may be made of, for example, tocopherol, butylhydroxyanisole, dibutylhydroxytoluene, phytic acid and the like. As examples of chelating agents blended in the cosmetics of the present invention depending on the purposes thereof, mention may be made of, for example, alanine, sodium salt of edetic acid, sodium polyphosphate, sodium metaphosphate, phosphoric acid and the like.

As examples of other humectant components blended in the cosmetics of the present invention depending on the purposes thereof, mention may be made of, for example, hyaluronic acid, chondroitin sulfate, pyrrolidone carboxylic acid salts, polyoxyethylene methylglucoside, polyoxypropylene methylglucoside, and the like. Needless to say, the aforementioned polyhydric alcohols exhibit a function of retaining moisture on the skin or hair.

The perfumes are not particularly restricted as long as they are lipophilic perfumes. As examples thereof, mention may be made of perfumes extracted from flowers, seeds, leaves, and roots of various plants; perfumes extracted from seaweeds; perfumes extracted from various parts or secretion glands of animals such as musk and sperm oil; or artificially synthesized perfumes such as menthol, musk, ethyl acetate, and vanilla. The perfumes are blended in the cosmetics in order to impart the cosmetics with a certain aroma or scent, or in order to mask unpleasant odor.

As examples of products of the cosmetics of the present invention, mention may be made of skin cosmetic products such as skin cleansing products, skin care products, makeup products, antiperspirant products, UV-ray protective products and the like; hair cosmetics such as hair cleansing products, hair styling products, hair coloring products, hair tonic products, hair rinse products, hair conditioner products, hair treatment products and the like; and cosmetics for use in bathing. In particular, in the cosmetics according to the present invention, a dry feeling derived from the volatile oil agents is prevented. Skin care products, hair cosmetic products, antiperspirant products, makeup products or UV-ray protective products are preferred. As examples of medicinal products of the present invention, mention may be made of hair regrowth products, hair restorers, pain relievers, bactericides, anti-inflammatory agents, fresheners, and skin anti-aging products, but not limited thereto.

The aforementioned cosmetics for use on skin can be used on various parts such as the scalp, face (including lips, eyebrows, and cheeks), fingers, nails, and the entire body. More particularly, as examples thereof, mention may be made of skin cleansing products such as cleansing gels, cleansing creams, cleansing foams, cleansing milks, cleansing lotions, facial cleansing creams, eye make-up removers, cleansing foams, liquid soaps (body soaps), hand soaps, gel soaps, bar soaps, facial rinses, body rinses, creams for use in shaving, nail polish removers, anti-acne products and the like; skin care products such as creams for use on skin, scalp treatments, skin milks, milky lotions, emulsions, cosmetic lotions, moisturizers, beautifying liquids, facial packs, body powders, essences, lotions for use in shaving, products for use in massaging and the like; makeup products such as foundations, liquid foundations, oil-based foundations, makeup bases, white powder, face powder, lipsticks, lip creams, lip colors, lip glosses, eye shadows, eyeliners, eye creams, eyebrow pencils, eyelash cosmetic products, eyebrow pencils, eyebrow brush, mascara, rouge, cheek cosmetic products (cheek color, cheek rouge), nail enamels, toe polish, nail color, nail lacquer, enamel remover, nail polish, and the like; antiperspirants such as deodorants and the like; UV-ray protective products such as sunscreen agents, suntanning drugs (suntanning agents) and the like.

As examples of the aforementioned hair cosmetics, mention may be made of hair cleansing agents such as shampoo, two-in-one shampoo and the like; hair styling products such as hair oil, hair wax, hair curl-retaining agents, setting agents, hair creams, hair spray, hair liquid and the like; hair coloring products such as hair dyes, hair color spray, hair color rinse, hair color stick and the like; hair growth products such as hair tonic, hair treatment, hair packs, and the like; and hair rinse or hair conditioning products such as oil rinse, cream rinse, treatment rinse, hair conditioners, hair treatments and the like. In addition, as examples of the aforementioned cosmetic for use in bathing, mention may be made of bath oil, bath salts, and foam bath products.

The forms of the cosmetics and the cosmetic products according to the present invention are not particularly restricted. The cosmetics and cosmetic products can be preferably in the form of liquids, W/O milky lotions, O/W milky lotions, W/O creams, O/W creams, solids, pastes, gels, powders, lamellas, mousses, mists, granules, flakes, grains and the like. The particularly preferable forms are W/O milky lotions, W/O creams, solids, pastes, gels, powders, lamellas, mousses, and mists.

The containers of the cosmetics or the cosmetic products according to the present invention are not particularly restricted. Any containers can be charged with the cosmetics and the cosmetic products, such as jars, pump cans, tubes, bottles, pressure spray containers, pressure-resistant aerosol containers, light-shield containers, compact containers, metal dishes, lipstick containers, dispensing containers, aerosol containers, partitioned containers with mixed fluid discharging ports, and the like. Conventional silicone-based formulations tend to be separated in tube containers, but the compositions for external use according to the present invention, particularly cosmetics, exhibit superior stability. For this reason, the compositions of the present invention possess an advantage in that they can be stably stored even in the aforementioned tube containers.

EXAMPLES

Hereinafter, the present invention is described in detail with reference to examples and comparative examples. It should be understood that the present invention is not restricted to the examples. In the following description, "%" and "parts" mean "% by weight" and "parts by weight", respectively, and the viscosity is a value measured at 25° C.

Example 1a

Preparation of 1,2-bis(pentamethyldisiloxy)ethane

A mixture of 100 g of a 33% solution of 1,2-bis(chlorodimethylsilyl)ethane in toluene and 10 g of water was reacted for 6 hours at 90° C. to completely hydrolyze the chlorosilane, and then cooled. A mixture of 375 g of hexamethyldisiloxane which was an excess amount and 0.1 g of trifluoromethanesulfonic acid was heated to 50° C., and the hydrolysate obtained above was added thereto dropwise, followed by aging for 2 hours. The obtained mixture was washed with water until the wash liquid exhibited neutrality. The resultant mixture was distilled. Thereby, 1,2-bis(pentamethyldisiloxy) ethane represented by the following formula:

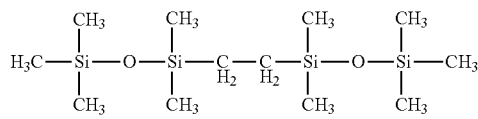

was obtained. The boiling point thereof was 109° C./20 torr and the yield was 29.8 g (yield=61%).

Example 1b

Preparation of 1,2-bis(pentamethyldisiloxy)ethane 294.9 g of hexamethyldisiloxane, 87.38 g of acetic acid and 0.13 g of trifluoromethanesulfonic acid were placed in a flask, and the mixture was heated to 45° C. 150 g of 1,2-bis(dimethylmethoxysilyl)ethane was added thereto dropwise. After the dropwise addition was completed, aging was carried out for one hour. It was confirmed that the raw materials had disappeared by means of gas chromatography. The obtained mixture was washed with water until the wash liquid exhibited neutrality. The resultant mixture was distilled. Thereby, 1,2-bis(pentamethyldisiloxy)ethane was obtained. The yield was 79.7 g (yield=34%).

1,2-bis(pentamethyldisiloxy)ethane synthesized in Example 1a and Example 1b was analyzed by means of gas chromatography. As a result, the purity was 99.2%. In addition, confirmation of the structure thereof was carried out by means of $^{29}$Si-NMR (δ: 7.09 (2Si); 8.52 (2Si)) and $^{13}$C-NMR (δ: −0.28 (4C); 2.04 (6C); 9.93 (2C)).

Example 2

Preparation of 1,1,3,3,6,6,8,8-octamethyl-2,7-dioxy-1,3,6,8-tetrasilacyclodecane Hydrolysis was carried out with 100 g of a 33% solution of 1,2-bis(chlorodimethylsilyl)ethane in toluene and 10 g of water, and aging was carried out for 6 hours at 90° C. The obtained mixture was washed with water until the wash liquid exhibited neutrality. The resultant mixture was distilled. Thereby, a large cyclic compound represented by the following formula:

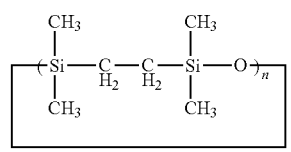

(wherein n=2) was obtained. The boiling point thereof was 125° C./20 torr, and the yield was 17.2 g (yield=35%).

Evaluation 1

Miscibility between 1,2-bis(pentamethyldisiloxy)ethane obtained in Example 1, 1,1,3,3,6,6,8,8-octamethyl-2,7-dioxy-1,3,6,8-tetrasilacyclodecane, dimethylpolysiloxane (SH200-2cs: viscosity=2 cs, manufactured by Dow Corning Toray Co., Ltd.), cyclopentasiloxane, or methyltrimethicone (hereinafter, simply referred to as "silicone component") and octyl paramethoxycinnamate as a representative UV-ray absorber was evaluated. The silicone component and octyl paramethoxycinnamate were mixed by varying the ratios of the silicone component/octyl paramethoxycinnamate=10/90, 50/50 and 90/10. The mixture was allowed to stand for 6 hours at room temperature. The outer appearance thereof was visually observed. The results are shown in Table 1.

TABLE 1

| Silicone component (% by weight) | 10 | 50 | 90 |
|---|---|---|---|
| 1,2-bis(pentamethyldisiloxyethane (Example 1) | dissolved | dissolved | dissolved |
| 1,1,3,3,6,6,8,8-octamethyl-2,7-dioxy-1,3,6,8-tetrasilacyclodecane (Example 2) | dissolved | dissolved | dissolved |
| Dimethylpolysiloxane (Comparative Example 1) | dissolved | separated | dissolved |
| Cyclopentasiloxane (Comparative Example 2) | dissolved | separated | dissolved |
| Methyltrimethicone (Comparative Example 3) | dissolved | separated | dissolved |

Evaluation 2

The silicone component was applied to back of the hand and the inner part of the forearm. The glossiness immediately after applying and after allowing to stand for a while was visually evaluated on the basis of the following evaluation criteria.

OO: indicating that glossiness was strongly exhibited.
O: indicating that glossiness was exhibited.
Δ: indicating that glossiness was slightly exhibited.
X: indicating that glossiness was not exhibited.

The results are shown in Table 2.

TABLE 2

| Silicone component (% by weight) | Glossiness |
|---|---|
| 1,2-bis(pentamethyldisiloxyethane (Example 1) | OO |
| 1,1,3,3,6,6,8,8-octamethyl-2,7-dioxy-1,3,6,8-tetrasilacyclodecane (Example 2) | OO |
| Dimethylpolysiloxane (Comparative Example 1) | Δ |
| Cyclopentasiloxane (Comparative Example 2) | Δ |
| Methyltrimethicone (Comparative Example 3) | Δ |

Evaluation 3

1,2-bis(pentamethyldisiloxy)ethane obtained in Example 1 was placed in a glass bottle, and stored for one week in a freezer at −5° C. Thereby, stability at low temperature was evaluated. For comparison, octamethylcyclotetrasiloxane (D4) and decamethylcyclopentasiloxane (D5) were also evaluated.

The results are shown in Table 3.

TABLE 3

| Silicone component (% by weight) | Outer appearance at 25° C. | After one week at −5° C. |
|---|---|---|
| Example 1 (1,2-bis(pentamethyldisiloxyethane) | liquid | liquid |
| Comparative Example 4 (octamethylcyclotetrasiloxane, D4) | liquid | solidified |
| Reference (Decamethylcyclopentasiloxane, D5) | liquid | liquid |

As shown in Table 3, it was confirmed that the organopolysiloxane of the present invention exhibited stability at low temperature which is equivalent to or superior to that of conventional volatile silicone D5 known as having superior stability at low temperature.

Example 3

Dry Feeling-Controlled Antiperspirant

An antiperspirant having a composition described below was prepared.
Composition:

| Oil Phase | |
|---|---|
| (1) 1,2-bis(pentamethyldisiloxy)ethane | 41.15% |
| (2) Cyclomethicone | 2.35% |
| (3) Cyclomethicone/dimethicone copolyol | 6.0% |
| (4) Isopropyl myristate | 4.5% |
| (5) PPG-3 myristyl ether | 4.5% |
| (6) Perfume | 1.0% |
| (7) Octylmethoxy cinnamate | 0.5% |
| Polar phase | |
| (8) Aluminum chlorohydrate (50% aqueous solution) | 40.0% |

More particularly, components 1 to 7 were uniformly mixed and dispersed. Subsequently, component 8 was mixed and dispersed therein.

Evaluation 4

Using the antiperspirant of Example 3 and a comparative antiperspirant prepared by replacing the entire amount of 1,2-bis(pentamethyldisiloxy)ethane in the antiperspirant of Example 3 with cyclomethicone, the sensation during use of the cosmetics was evaluated by 20 panelists in view of a property of spreading on skin during use and a property of controlling a dry feeling after application.

The comparison evaluation was carried out on the basis of the following two points:
(1) whether or not a property of spreading the antiperspirant on the skin during use was good.
(2) whether or not a dry feeling was felt after application.

"Dry feeling" means that a panelist feels a negative sensation during use such as a dry feeling to the touch (sometimes expressed by "dryness") a dry sensation or de-sebum sensation on the skin, immediately after application or some time after application. When dry feeling is controlled, a more preferable sensation during use is realized. In the following table, the results of comparison evaluation carried out by 20 panelists are shown.

TABLE 4

| | Antiperspirant of Example 3 | Comparative antiperspirant |
|---|---|---|
| Good spreading property was exhibited on the skin during use and superior feeling to the touch was exhibited. | 18 panelists | 2 panelists |
| Dry feeling after application was not felt. | 17 panelists | 3 panelists |

As shown in Table 4, the antiperspirant of Example 3 was evaluated as having better spreading properties on the skin, compared with the comparative antiperspirant by the most panelists. In addition, the antiperspirant of Example 3 was evaluated as having a more preferable sensation during use such as moisturizingly spreading on the skin without a dry feeling, compared with the comparative antiperspirant.

As described above, it was confirmed that the antiperspirant of Example 3 was remarkably superior to the comparative antiperspirant in view of both a property of spreading during use and a property of controlling a dry feeling after application.

In the following description, composition examples and preparation examples of the cosmetics of the present invention are described in detail.

Composition Example 1

O/W Soap-Emulsion Type [Part(s)]

| (1) Stearic acid | 1 |
|---|---|
| (2) Polysorbate 80 | 0.3 |
| (3) Sorbitan sesquioleate | 0.2 |
| (4) Glyceryl stearate | 0.2 |
| (5) Cetanol | 1.5 |
| (6) Pentaerythtyl tetraoctanoate | 2 |
| (7) Organopolysiloxane of general formula (1) or (2) | 5 |
| (8) Mineral oil | 1 |
| (9) Water | 55.25 |
| (10) DPG | 8 |
| (11) Glycerol | 4 |
| (12) Methylisothiazolinone | 0.05 |
| (13) Triethanolamine | 0.5 |
| (14) Carbomer | 21 |

Preparation Steps

1. Components 1 to 8 are uniformly mixed and dissolved at 70° C.
2. Components 9 to 13 are uniformly mixed, and dissolved at 70° C.
3. The aqueous liquid obtained in step 2 is gradually added to the oil-based liquid obtained in step 1 at 70° C.
4. Component 14 is added to the emulsion obtained in step 3, followed by cooling.

5. The aqueous liquid obtained in step 3 is added to the oil-based dispersion obtained in step 4, and the mixture is emulsified.

Composition Example 2

W/O Type Cream Cosmetic [Part(s)]

| | | |
|---|---|---|
| (1) | PEG/PPG-19/19 dimethicone | 1 |
| (2) | Oranopolysiloxane of general formula (1) or (2) | 10.5 |
| (3) | Dimethicone 6 cs | 6 |
| (4) | PCA dimethicone | 1 |
| (5) | Tocopherol acetate | 0.2 |
| (6) | Dimethicone cross polymer*[1] | 1 |
| (7) | Cyclopentasiloxane | 0.5 |
| (8) | Purified water | 67.75 |
| (9) | Magnesium L-ascorbyl phosphate | 3 |
| (10) | Sodium citrate | 1 |
| (11) | Glycerol | 8 |
| (12) | Methylisothiazoline | 0.05 |

*[1]DC9040 (Dow Corning Corporation)

Preparation Steps

1. Components 6 and 7 are uniformly mixed and dispersed.
2. Components 8 to 10 are uniformly mixed and dissolved.
3. Components 11 and 12 are added to the aqueous liquid obtained in step 2, and the mixture is uniformly mixed and dissolved.
4. Components 1 to 5 are added to the oil-based dispersion obtained in step 1, and the mixture is uniformly mixed and dispersed.
5. The aqueous liquid obtained in step 3 is added to the oil-based dispersion obtained in step 4, and the mixture is emulsified.

Composition Example 3

Liquid Foundation (W/O) [Part(s)]

| | | |
|---|---|---|
| (1) | Lauryl PEG/PPG-18/18 dimethicone*[1] | 10 |
| (2) | Organopolysiloxane of general formula (1) or (2) | 20 |
| (3) | Dimethicone crosspolymer*[2] | 5 |
| (4) | Ethylhexyl 2-ethylhexanoate | 5 |
| (5) | Octylsilane-treated red iron oxide | 0.1 |
| (6) | Octylsilane-treated yellow iron oxide | 0.6 |
| (7) | Mica | 3.5 |
| (8) | Octylsilane-treated black iron oxide | 0.05 |
| (9) | Purified water | remainder |
| (10) | Polysorbate 20 | 0.2 |
| (11) | Preservatives | 0.5 |
| (12) | Xanthan gum | 0.5 |
| (13) | Magnesium sulfate | 0.4 |

*[1]DC5200 Formulation Aid (Dow Corning Corporation)
*[2]DC9040 (Dow Corning Corporation)

Preparation Steps

1. Components 1 to 8 are mixed and sufficiently dispersed.
2. Components 9 to 13 are uniformly mixed and dispersed.
3. The aqueous dispersion obtained in step 2 is added to the oil-based dispersion obtained in step 1, and the mixture is emulsified.

Composition Example 4

Liquid Foundation (O/W) [Part(s)]

| | | |
|---|---|---|
| (1) | Stearic acid | 2.4 |
| (2) | Propylene glycol monostearate | 2.0 |
| (3) | Cetyl alcohol | 0.2 |
| (4) | Liquid lanolin | 2 |
| (5) | Liquid paraffin | 1 |
| (6) | Organopolysiloxane of general formula (1) or (2) | 2 |
| (7) | Isopropyl myristate | 8.5 |
| (8) | Purified water | remainder |
| (9) | Sodium carboxymethylcellulose | 0.2 |
| (10) | Bentonite | 0.5 |
| (11) | Dipropylene glycol | 4.0 |
| (12) | Triethanolamine | 1.1 |
| (13) | Preservatives | q.s. |
| (14) | Titanium oxide | 8 |
| (15) | Mica | 4.0 |
| (16) | Coloring pigments | q.s. |
| (17) | Perfume | q.s. |

Preparation Steps

1. Components 8 to 16 are sufficiently mixed and dispersed at 75° C.
2. Components 1 to 7 are mixed at 80° C.
3. The oil-based mixture obtained in step 2 is added to the aqueous mixture obtained in step 1 at 75° C., and the mixture is emulsified followed by cooling to room temperature.

Composition Example 5

Sunscreen Emulsion (W/O) [Part(s)]

| | | |
|---|---|---|
| (1) | Ethylhexyl paramethoxycinnamate | 5 |
| (2) | Silicone-treated titanium oxide | 5 |
| (3) | Silicone-treated zinc oxide | 9 |
| (4) | Squalane | 20 |
| (5) | Organopolysiloxane of general formula (1) or (2) | 13.0 |
| (6) | Dimethicone (2 cs) | 10 |
| (7) | Cyclopentasiloxane/acrylates/polytrimethylsiloxymethacrylate copolymer*[1] | 2 |
| (8) | Glycerol diisostearate | 2.0 |
| (9) | Polyether-modified silicone*[2] | 0.5 |
| (10) | Organo-modified montmorillonite | 0.5 |
| (11) | Purified water | remainder |
| (12) | 1,3-butylene glycol | 5 |

*[1]FA4001CM Silicone Acrylate (Dow Corning Toray Co,. Ltd.)
*[2]SS-2910 (Dow Corning Toray Co,. Ltd.)

Preparation Steps

1. Components 1 to 10 are heated to 60° C., and uniformly mixed and dissolved.
2. Components 11 and 12 are gradually added to the oil-based liquid obtained in step 1, and the mixture is emulsified.

Composition Example 6

Sunscreen Cream (W/O) [Part(s)]

| | | |
|---|---|---|
| (1) | Titanium oxide slurry | 40 |
| (2) | Octyl methoxycinnamate | 10 |
| (3) | Organopolysiloxane of general formula (1) or (2) | 5 |
| (4) | Caprylmethicone | 3 |
| (5) | Trimethylsiloxysilicic acid | 7.5 |
| (6) | Dimethicone 6 cs | 4.5 |
| (7) | PEG-10 dimethicone*[1] | 1 |
| (8) | Silica | 2.5 |
| (9) | Purified water | 26.45 |
| (10) | Methylisothiazolinone | 0.05 |

*[1]SS-2910 (Dow Corning Toray Co., Ltd.)

Preparation Steps

1. Components 1 to 8 are uniformly mixed and dispersed.
2. Components 9 and 10 are mixed and dissolved.
3. The aqueous liquid obtained in step 2 is added to the oil-based dispersion obtained in step 1, and the mixture is emulsified.

Composition 7

Lip Gloss [Part(s)]

| | | |
|---|---|---|
| (1) | Polyamide-modified silicone[1]* | 19 |
| (2) | Organopolysiloxane of general formula (1) or (2) | 10 |
| (3) | Methylphenyl-modified silicone | 28 |
| (4) | Isopropyl palmitate | 38 |
| (5) | Trioctanoine | 2 |
| (6) | Titanium oxide | 3 |

[1]*2-8178 gellant (Dow Corning Corporation

Preparation Steps

All components are heated and mixed at 100° C., and a container is charged with the mixture. Thereby, a lip gloss product is obtained.

Composition Example 8

Hair Wax [Part(s)]

| | | |
|---|---|---|
| (1) | Polyamide-modified silicone*[1] | 18 |
| (2) | Organopolysiloxane of general formula (1) or (2) | 35 |
| (3) | Glycerol tri(caprylate/caprate) | remainder |
| (4) | Red No. 225 | 0.001 |
| (5) | Ethanol | 0.5 |

Note
*[1]2-8178 gellant (Dow Corning Corporation)

Preparation Steps

1. Components 1 to 3 are mixed, and then heated and dissolved at 100° C., followed by cooling to 60° C.
2. A mixture of components 4 and 5 is added to the oil-based liquid obtained in step 1, and a container is charged with the mixture. Thereby, a hair wax product is obtained.

Composition Example 9

Antiperspirant [Part(s)]

| | | |
|---|---|---|
| (1) | Polyamide-modified silicone | 12 |
| (2) | Trimethylsiloxysilicic acid | 2.5 |
| (3) | Behenoxydimethicone (Abil WAX 2440) | 2.5 |
| (4) | Organopolysiloxane of general formula (1) or (2) | 29.37 |
| (5) | Phenyltrimethicone | 10.0 |
| (6) | Isostearyl alcohol (Prisorine) | 0.50 |
| (7) | Purified water | remainder |
| (8) | Al Zr tetrahydrex glycine | 20.00 |
| (9) | Polysorbate 20 | 1 |

Preparation Steps

1. Components 1 to 6 are uniformly mixed and dispersed.
2. Components 7 to 10 are mixed and dispersed.
3. The aqueous dispersion obtained in step 2 is added to the oil-based dispersion obtained in step 1, and then mixed.

The invention claimed is:

1. A method of improving the touch or glossiness of a cosmetic by adding to the cosmetic 1 to 99% by weight of an organopolysiloxane represented by the following formula (1) or (2):

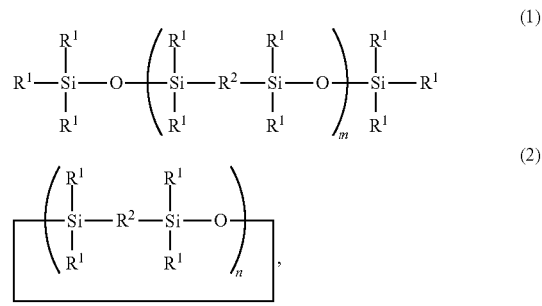

wherein the organopolysiloxane of formula (1) is 1,2-bis (pentamethyldisiloxy) ethane;
wherein the organopolysiloxane of formula (2) is 1,1,3,3, 6,6,8,8-octamethyl-2,7-dioxy-1,3,6,8-tetrasilacyclodecane;
wherein the cosmetic further comprises: at least one additional component selected from the group consisting of at least one oil agent other than the organopolysiloxane of formula (1) or (2), an anionic surfactant, a cationic surfactant, a nonionic surfactant and an amphoteric surfactant; and
at least one cosmetic raw material selected from the group consisting of a powder, a coloring agent, water-soluble polymers, oil-soluble gelling agents, silicone resins, silicone elastomers, organo-modified silicones, organo-modified clay minerals, and a UV-ray protective component.

2. The method according to claim 1, wherein the cosmetic comprises both the organopolysiloxane represented by formula (1) and the organopolysiloxane represented by formula (2).

3. The method according to claim 1, wherein the oil agent is a silicone oil.

4. The method according to claim 3, wherein the silicone oil is a hydrophobic silicone oil having a viscosity at 25° C. ranging from 0.65 to 100,000 mm²/s.

5. The method according to claim 3, wherein the silicone oil is an organopolysiloxane represented by the following general formula (3), (4) or (5):

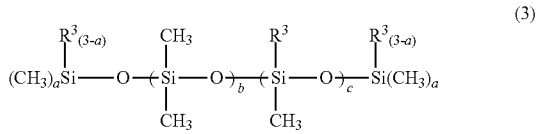

wherein
R³ is a hydrogen atom, a hydroxyl group or a group selected from monovalent non-substituted or fluorine- or amino-substituted, C₁₋₃₀ alkyl groups, aryl groups, alkoxy groups and groups represented by (CH₃)₃SiO{(CH₃)₂SiO}₁Si(CH₃)₂CH₂CH₂—, wherein l is an integer ranging from 0 to 1,000;
a is an integer ranging from 0 to 3;
b is an integer ranging from 0 to 1,000; and
c is an integer ranging from 0 to 1,000, with the proviso that 1<b+c<2,000,

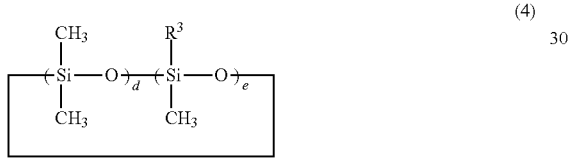

wherein
R³ is the same as defined above;
d is an integer ranging from 0 to 8; and
e is an integer ranging from 0 to 8, with the proviso that 3<d+e<8,

wherein
R³ is the same as defined above;
f is an integer ranging from 1 to 4; and
g is an integer ranging from 0 to 500.

6. The method according to claim 1, wherein the at least one cosmetic raw material comprises powder and/or a coloring agent.

7. The method according to claim 6, wherein the powder is at least one powder selected from the group consisting of inorganic pigment powders, organic pigment powders and resin powders, wherein the powder has an average particle size ranging from 1 nm to 20 μm.

8. The method according to claim 6, wherein at least one part of the powder and/or coloring agent is subjected to a hydrophobic treatment.

9. The method according to claim 1, wherein the at least one cosmetic raw material comprises at least one material selected from the group consisting of water-soluble polymers, oil-soluble gelling agents and organo-modified clay minerals.

10. The method according to claim 1, wherein the at least one cosmetic raw material comprises at least one material selected from the group consisting of silicone resins, silicone elastomers and organo-modified silicones.

11. The method according to claim 1, wherein the at least one cosmetic raw material comprises a UV-ray protective component.

12. The method according to claim 1, wherein the cosmetic is selected from the group consisting of a skin care product, a hair product, an antiperspirant product, a deodorant product, a makeup product and a UV-ray protective product.

13. A cosmetic comprising: 1 to 99% by weight of an organopolysiloxane represented by the following formula (1) or (2):

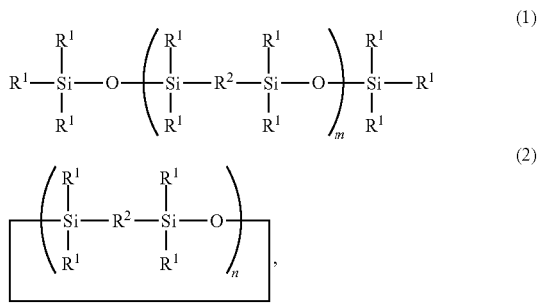

wherein the organopolysiloxane of formula (1) is 1,2-bis (pentamethyldisiloxy) ethane;
wherein the organopolysiloxane of formula (2) is 1,1,3,3, 6,6,8,8-octamethyl-2,7-dioxy-1,3,6,8-tetrasilacyclodecane;
wherein the cosmetic further comprises: at least one additional component selected from the group consisting of at least one oil agent other than the organopolysiloxane of formula (1) or (2), an anionic surfactant, a cationic surfactant, a nonionic surfactant and an amphoteric surfactant; and
at least one cosmetic raw material selected from the group consisting of a powder, a coloring agent, water-soluble polymers, oil-soluble gelling agents, silicone resins, silicone elastomers, organo-modified silicones, organo-modified clay minerals, and a UV-ray protective component.

14. The cosmetic composition according to claim 13, wherein the organopolysiloxane is according to formula (1).

15. The cosmetic composition according to claim 13, wherein the organopolysiloxane is according to formula (2).

16. The cosmetic composition according to claim 13, wherein the oil agent is a silicone oil.

17. The cosmetic composition according to claim 16, wherein the silicone oil is a hydrophobic silicone oil having a viscosity at 25° C. ranging from 0.65 to 100,000 mm²/s.

18. The cosmetic composition according to claim 16, wherein the silicone oil is an organopolysiloxane represented by the following general formula (3), (4) or (5):

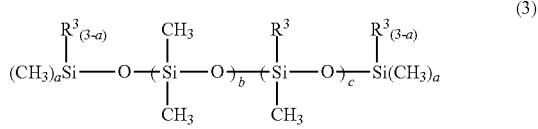

wherein
R³ is a hydrogen atom, a hydroxyl group or a group selected from monovalent non-substituted or fluorine- or amino-substituted, C₁₋₃₀ alkyl groups, aryl groups, alkoxy groups and groups represented by $(CH_3)_3SiO\{(CH_3)_2SiO\}_lSi(CH_3)_2CH_2CH_2$—, wherein l is an integer ranging from 0 to 1,000;
a is an integer ranging from 0 to 3;
b is an integer ranging from 0 to 1,000; and
c is an integer ranging from 0 to 1,000, with the proviso that $1 \leq b+c \leq 2,000$,

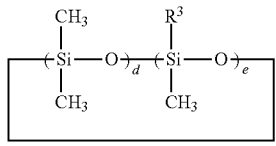
(4)

wherein
$R^3$ is the same as defined above;
d is an integer ranging from 0 to 8; and
e is an integer ranging from 0 to 8, with the proviso that $3 \leq d+e \leq 8$, $$R^3_{(4-f)}Si(OSiCH_3)_g \quad (5)$$

wherein
$R^3$ is the same as defined above;
f is an integer ranging from 1 to 4; and
g is an integer ranging from 0 to 500.

19. The cosmetic composition according to claim 13, wherein the powder is at least one powder selected from the group consisting of inorganic pigment powders, organic pigment powders and resin powders, having an average particle size ranging from 1 nm to 20 μm.

20. The cosmetic composition according to claim 13, wherein at least one part of said powder and/or coloring agent is subjected to a hydrophobic treatment.

21. The cosmetic composition according to claim 13, wherein the cosmetic composition is in the form of a skin care product, a hair product, an antiperspirant product, a deodorant product, a makeup product or a UV-ray protective product.

* * * * *